(12) United States Patent
Geng

(10) Patent No.: US 12,351,651 B2
(45) Date of Patent: Jul. 8, 2025

(54) POLYPEPTIDE FOR REPAIRING MUCOSAL DAMAGE OR SKIN WOUND AND USE THEREOF

(71) Applicant: Sichuan Gooddoctor Panxi Pharmaceutical Co., Ltd., Xichang (CN)

(72) Inventor: Funeng Geng, Xichang (CN)

(73) Assignee: Sichuan Gooddoctor Panxi Pharmaceutical Co., Ltd., Xichang (CN)

( * ) Notice: Subject to any disclaimer, the term of this patent is extended or adjusted under 35 U.S.C. 154(b) by 243 days.

(21) Appl. No.: 18/013,344

(22) PCT Filed: Jul. 1, 2021

(86) PCT No.: PCT/CN2021/103943
§ 371 (c)(1),
(2) Date: Dec. 28, 2022

(87) PCT Pub. No.: WO2022/002186
PCT Pub. Date: Jan. 6, 2022

(65) Prior Publication Data
US 2023/0295233 A1    Sep. 21, 2023

(30) Foreign Application Priority Data
Jul. 1, 2020  (CN) .......................... 202010619687.2

(51) Int. Cl.
| C07K 7/08 | (2006.01) |
| A61K 38/00 | (2006.01) |
| A61P 1/02 | (2006.01) |
| A61P 1/04 | (2006.01) |
| C07K 5/103 | (2006.01) |
| C07K 5/117 | (2006.01) |
| C07K 7/06 | (2006.01) |

(52) U.S. Cl.
CPC .................... C07K 7/08 (2013.01); A61P 1/02 (2018.01); A61P 1/04 (2018.01); C07K 5/101 (2013.01); C07K 5/1024 (2013.01); C07K 7/06 (2013.01); A61K 38/00 (2013.01)

(58) Field of Classification Search
CPC .............. C07K 7/08; A61P 1/02; A61K 38/00
See application file for complete search history.

(56) References Cited

U.S. PATENT DOCUMENTS

| 6,214,795 B1 | 4/2001 | Benjamin et al. |
| 10,369,204 B2* | 8/2019 | Schøller ............ C07K 14/70539 |
| 2012/0258126 A1* | 10/2012 | Scholler ............... A61K 47/646 |
| | | 424/190.1 |
| 2013/0330335 A1* | 12/2013 | Bremel .................. G16B 20/00 |
| | | 435/69.6 |
| 2020/0000868 A1 | 1/2020 | Chen et al. |

FOREIGN PATENT DOCUMENTS

| CN | 107973838 A | 5/2018 | |
| CN | 108503690 A | 9/2018 | |
| CN | 108715600 A | 10/2018 | |
| CN | 110903348 A | 3/2020 | |
| WO | 1998/21237 A2 | 5/1998 | |
| WO | 2007/002469 A2 | 1/2007 | |
| WO | WO 2007/002469 * | 1/2007 | ............. A61K 38/18 |
| WO | WO2009126037 A1 | 10/2009 | |

OTHER PUBLICATIONS

International Search Report and Written Opinion for Application No. PCT/CN2021/103943, dated Sep. 28, 2021, 13 pages.
Tsuda et al., Poststatin, a new inhibitor of prolyl endopeptidase. VIII. Endopeptidase inhibitory activity of non-peptidyl poststatin analogues, The Journal of Antibiotics, 49(9):900-908, 1996.
Van Baalen et al., Kinetics of Antiviral Activity by Human Immunodeficiency Virus Type 1-Specific Cytotoxic T Lymphocytes (CTL) and Rapid Selection of CTL Escape Virus In Vitro, Journal of Virology, 72(8):6851-57, 1998.

* cited by examiner

*Primary Examiner* — Amber D Steele
(74) *Attorney, Agent, or Firm* — Travis Young; Bozicevic, Field & Francis LLP

(57) ABSTRACT

Provided are a new polypeptide for repairing mucosal damage or a skin wound, and the use thereof. The polypeptide is not homologous with known polypeptides, can be stably present in vivo and in vitro, and has the effect of regulating stem cell proliferation and differentiation to repair mucosal damage or a skin wound. The present invention further relates to the use of the new polypeptide in the repairing of mucosal damage or a skin wound by means of regulating stem cell proliferation and differentiation, and the use thereof in the prevention, alleviation or treatment of gastrointestinal diseases.

11 Claims, 5 Drawing Sheets

Specification includes a Sequence Listing.

POLYPEPTIDE FOR REPAIRING MUCOSAL DAMAGE OR SKIN WOUND AND USE THEREOF

CROSS-REFERENCE TO RELATED APPLICATIONS

This application is a 35 U.S.C. § 371 national stage filing of International Application No. PCT/CN2021/103943 filed on Jul. 1, 2021, which in turn claims priority to Chinese Patent Application No. 202010619687.2, filed on Jul. 1, 2020. The entire contents of each of the foregoing applications are expressly incorporated herein by reference.

SEQUENCE LISTING

This instant application contains a Sequence Listing which has been submitted electronically in ASCII format and is hereby incorporated by reference in its entirety. Said ASCII copy, created on Mar. 3, 2023, is named 138106_00102_SL.txt and is 16,605 bytes in size.

TECHNICAL FIELD

Provided is a novel polypeptide for repairing mucosal damage or skin wounds and the use thereof. The polypeptide provided herein has no homology with any known polypeptides, can exist stably both in vivo and in vitro, and has the effect of regulating the proliferation and differentiation of stem cells to repair mucosal damage or skin injury. In addition, provided is the use of the novel polypeptide in repairing mucosal damage or skin wounds by regulating the proliferation and differentiation of stem cells and in preventing, alleviating or treating a gastrointestinal disease.

REFERENCE TO AN ELECTRONIC SEQUENCE LISTING

The contents of the electronic sequence listing (WUFZ-015_sequence listing.xml; Size: 94,716 bytes; and Date of Creation: Apr. 28, 2025) is herein incorporated by reference in its entirety.

BACKGROUND ART

Skin wounds and/or mucosal damage are common pathological characteristics of many diseases. Skin wounds or skin injury refers to damage to normal skin (tissue) caused by external injury-causing factors such as surgery, external forces, heat, electric current, chemicals and low temperatures and internal factors in the body such as local blood supply disturbance. Skin injury is often accompanied by the destruction of skin integrity and loss of a certain amount of normal tissues; in addition, the normal function of the skin is impaired. It is also referred to as a wound or trauma. At present, proteins/polypeptide drugs, including basic fibroblast growth factor, epidermal growth factor, platelet growth factor, granulocyte-macrophage colony-stimulating factor, growth hormone, etc., have obvious wound healing, skin care, anti-wrinkle, and anti-aging effects. However, these proteins/polypeptide drugs have relatively long amino acid sequences, leading to the disadvantages of high preparation cost and poor stability, so the application thereof is limited to some extent.

Human mucosa refers to the inner layers of the respiratory system, digestive system, genitourinary system and other cavities or cystic muscular organs. It is the second largest barrier in the human body after skin and includes the oral cavity, pharynx, trachea, esophagus, stomach, intestine, vagina, bladder, etc. The tube walls or bladder walls of these organs all have the same stratification rules and also have characteristics that are compatible with the functions thereof. The embryonic origins, tissue structures, pathological processes, clinical manifestations, prognosis etc. thereof all have common characteristics.

Chronic gastritis is a chronic inflammation of gastric mucosa, which is a common and frequently occurring disease in gastroenterology. Clinically, chronic inflammation of gastric mucosa caused by various causes (i.e., manifested as infiltration of monocytes and lymphocytes in pathology) and (or) glandular atrophic lesions are called chronic gastritis. Chronic atrophic gastritis (CAG), which is characterized by atrophy of gastric mucosa epithelium and glands, has a hidden onset, long course, non-specific symptoms, is difficult to cure, accounts for 11-31% among chronic gastritis, and it is common in middle-aged and elderly people. The onset thereof is associated with age and has nothing to do with gender. The disease has a slow onset, a lingering tendency, slow recovery, and treatment difficulties. Chronic atrophic gastritis is an important stage in the occurrence and development of gastric cancer and is regarded as a gastric precancerous lesion. In 1978, the World Health Organization (WHO) classified CAG as a precancerous state, which is often accompanied by precancerous lesions such as pseudopyloric metaplasia and intestinal metaplasia or atypical hyperplasia phase. Especially for those with diffuse intestinal metaplasia or atypical hyperplasia, canceration is more likely to occur. Most professionals in the field agree with the development mode of chronic superficial gastritis, atrophic gastritis, intestinal metaplasia, dysplasia and intestinal gastric cancer. Therefore, early accurate diagnosis and treatment are of great significance to patients with chronic atrophic gastritis. At present, modern medicine mainly treats this disease by means of symptom improvement and surgical intervention, and there is yet no good strategy for gland atrophy and intestinal metaplasia. CAG is an important stage for the transformation of chronic gastritis into gastric cancer. Active treatment of CAG is of far-reaching significance to prevent its canceration and reduce the incidence of gastric cancer. Seeking for an effective method for treating atrophic gastritis is one of the important measures to better prevent gastric cancer.

Clinically, mucosal tissue injuries may lead to gastrointestinal diseases such as chronic gastritis and digestive tract ulcers. There are two different mechanisms for mucosal epithelium repair, i.e., restitution and regeneration or renewal (Cur. Med. Chem., 2008, 15, 3133-3144). Restitution or recovery generally begins within a few minutes after injury, and superficial lesions are quickly repaired by cell migration. Regeneration refers to continuous regeneration through differentiation and proliferation of stem cells and progenitor cells, which lasts for several days to several months.

Epidermal growth factor (EGF) is a polypeptide composed of 53 amino acid residues, which widely exists in various tissues, organs and body fluids and can promote epithelial cell proliferation to protect the skin. Epidermal growth factor mainly promotes the proliferation and growth of skin tissue cells, so that new cells can replace aging cells, thus having anti-aging, skin care and health care functions, etc. Epidermal growth factor has been reported to have the function of repairing wounds. When skin wounds need to be disinfected and debrided, disinfectants containing iodine or hydrogen peroxide will be used, and as a result, EGF is unstable under this condition. Growth factors are related to healing from gastrointestinal anastomosis (J. Surgical Res. 2014; 17:202-210); however, when EGF is orally administered through the gastrointestinal tract, it degrades after entering the body and cannot achieve therapeutic effects.

Therefore, there is a need for a peptide substance which is stable in vivo and in vitro and can treat skin and/or mucosal damage, especially gastrointestinal mucosal damage.

SUMMARY OF THE INVENTION

In order to overcome the deficiencies and defects in the prior art, an object of the present invention is to provide a novel class of polypeptides.

In a first aspect, provided is a compound of Formula (I) or a physiologically compatible salt thereof, wherein the compound of Formula (I) is as follows:

$$\text{H-Xaa}_1\text{-Xaa}_2\text{-Xaa}_3\text{-Xaa}_4\text{-Xaa}_5\text{-Val-Xaa}_6\text{-Xaa}_7\text{-Xaa}_8\text{-Xaa}_9\text{-Xaa}_{10}\text{-Xaa}_{11}\text{-OH} \quad (I)$$

wherein
$Xaa_1$ is Pro, Gly, Ala or absent;
$Xaa_2$ is Ala, Leu, Ile, Gly, Cys, Ser or absent;
$Xaa_3$ is Ala, Pro, Gly, Leu, Ile, Cys, Ser or absent;
$Xaa_4$ is Glu, Gln, Asp, Asn, Leu, Ile, Val or absent;
$Xaa_5$ is Pro, Gly, Ala, Val or absent;
$Xaa_6$ is Pro, Gly or Ala;
$Xaa_7$ is Leu, Phe, Val, Ala, Tyr, Glu, Lys, Asp, Ile, Met or absent;
$Xaa_8$ is Val, Leu, Gln, Ile, Met or absent;
$Xaa_9$ is Lys, Arg, His, Asp, Val or absent;
$Xaa_{10}$ is Glu, Gln, Asp, Asn or absent; and
$Xaa_{11}$ is Glu, Asp, Asn, Gln or absent, provided that at most 9 of $Xaa_1$, $Xaa_2$, $Xaa_3$, $Xaa_4$, $Xaa_5$, $Xaa_7$, $Xaa_8$, $Xaa_9$, $Xaa_{10}$ and $Xaa_{11}$ are absent.

In one embodiment, $X_{aa5}$ is Pro.
In one embodiment, $X_{aa6}$ is Pro.
In one embodiment, $X_{aa7}$ is Leu.
In one embodiment, the compound of Formula (I) has a structure of the following Formula (II):

$$\text{H-Xaa}_1\text{-Xaa}_2\text{-Xaa}_3\text{-Xaa}_4\text{-Pro-Val-Pro-Leu-Xaa}_8\text{-Xaa}_9\text{-Xaa}_{10}\text{-Xaa}_{11}\text{-OH} \quad (II),$$

wherein
$Xaa_1$ is Pro, Gly, Ala or absent;
$Xaa_2$ is Ala, Leu, Ile, Gly, Cys, Ser or absent;
$Xaa_3$ is Ala, Pro, Gly, Leu, Ile, Cys, Ser or absent;
$Xaa_4$ is Glu, Gln, Asp, Asn, Leu, Ile, Val or absent;
$Xaa_5$ is Val, Leu, Gln, Ile, Met or absent;
$Xaa_9$ is Lys, Arg, His, Asp, Val or absent;
$Xaa_{10}$ is Glu, Gln, Asp, Asn or absent; and
$Xaa_{11}$ is Glu, Asp, Asn, Gln or absent.

In one embodiment, $Xaa_1$ in Formula (I) or (II) is Pro or absent; preferably Pro.

In one embodiment, $Xaa_2$ in Formula (I) or (II) is Ala or absent; preferably Ala.

In one embodiment, $Xaa_3$ in Formula (I) or (II) is Ala, Gly or absent; preferably Ala.

In one embodiment, $Xaa_4$ in Formula (I) or (II) is Glu, Gln, Asp or absent; preferably Glu, Asp or Gln.

In one embodiment, $Xaa_8$ in Formula (I) or (II) is Val or absent; preferably Val.

In one embodiment, $Xaa_9$ in Formula (I) or (II) is Lys, Arg or absent; preferably Lys or absent.

In one embodiment, $Xaa_{10}$ in Formula (I) or (II) is Glu, Gln or absent; preferably Gln.

In one embodiment, $Xaa_{11}$ in Formula (I) or (II) is Asp or absent; preferably Asp.

In one embodiment, one of $Xaa_1$, $Xaa_2$, $Xaa_3$ and $Xaa_4$ in Formula (I) or (II) is absent; or two of $Xaa_1$, $Xaa_2$, $Xaa_3$ and $Xaa_4$ in Formula (I) or (II) are absent; or three of $Xaa_1$, $Xaa_2$, $Xaa_3$ and $Xaa_4$ in Formula (I) or (II) are absent; or all of $Xaa_1$, $Xaa_2$, $Xaa_3$ and $Xaa_4$ in Formula (I) or (II) are absent.

In one embodiment, one of $Xaa_8$, $Xaa_9$, $Xaa_{10}$ and $Xaa_{11}$ in Formula (I) or (II) is absent; or two of $Xaa_8$, $Xaa_9$, $Xaa_{10}$ and $Xaa_{11}$ in Formula (I) or (II) are absent; or three of $Xaa_8$, $Xaa_9$, $Xaa_{10}$ and $Xaa_{11}$ in Formula (I) or (II) are absent; or all of $Xaa_8$, $Xaa_9$, $Xaa_{10}$ and $Xaa_{11}$ in Formula (I) or (II) are absent.

In one embodiment, the compound is selected from any one of Compounds 1-73 of the present invention.

In one embodiment, the compound is selected from:
Pro-Ala-Ala-Glu-Pro-Val-Pro-Leu-Val-Lys-Gln-Asp (SEQ ID NO: 1);
Pro-Ala-Ala-Glu-Pro-Val-Pro-Leu-Val-Lys (SEQ ID NO: 3);
Pro-Ala-Ala-Gln-Pro-Val-Pro-Leu-Val-Lys-Gln-Asp (SEQ ID NO: 10);
Pro-Ala-Ala-Glu-Pro-Val-Pro-Leu (SEQ ID NO: 26);
Ala-Glu-Pro-Val-Pro-Leu-Val-Lys-Gln-Asp (SEQ ID NO: 27);
Ala-Glu-Pro-Val-Pro-Leu (SEQ ID NO: 30);
Glu-Pro-Val-Pro-Leu (SEQ ID NO: 31);
Pro-Val-Pro-Leu (SEQ ID NO: 32);
Pro-Val-Pro-Leu-Val-Lys-Gln-Asp (SEQ ID NO: 28);
Pro-Ala-Ala-Asp-Pro-Val-Pro-Leu-Val-Lys-Gln-Asp (SEQ ID NO: 11);
Pro-Ala-Gly-Glu-Pro-Val-Pro-Leu-Val-Lys-Gln-Asp (SEQ ID NO: 48);
Pro-Ala-Ala-Glu-Pro-Val-Pro-Leu-Val-Lys-Glu-Asp (SEQ ID NO: 57); or
Glu-Pro-Val-Pro-Leu-Val-Lys-Gln-Asp (SEQ ID NO: 38).

For convenience, when the compound of the present invention is described in the present application, H on the left side and OH on the right side are omitted.

In one embodiment, the compound is Pro-Ala-Ala-Glu-Pro-Val-Pro-Leu-Val-Lys-Gln-Asp (SEQ ID NO: 1).

In a second aspect, provided is a method for repairing mucosal damage, the method comprising administering the compound of the present invention or a physiologically compatible salt thereof to a subject or bringing the mucosal damage into contact with the compound of the present invention or the physiologically compatible salt thereof. In one embodiment, the repair is carried out by regulating the proliferation and differentiation of stem cells.

In one embodiment, the mucosal damage is mucosal damage in a cavity such as the digestive system or respiratory system.

The mucosal damage of the digestive system is related to oral, esophageal and gastrointestinal diseases, and oral diseases include oral ulcer, stomatitis, gingivitis, periodontitis, etc.; the esophageal diseases include esophagitis, esophageal ulcer, etc.; and the gastrointestinal diseases include, without limitation, chronic gastritis, chronic atrophic gastritis, acute gastritis, gastroduodenal ulcer, functional gastrointestinal diseases, dyspepsia, precancerous lesions, digestive system tumors, gastrointestinal bleeding, gastroesophageal reflux disease, acute and chronic enteritis, ulcerative colitis, Crohn's disease, and mucosal injuries caused by radiotherapy and/or chemotherapy.

In a preferred embodiment, the digestive tract mucosa includes gastric mucosa and intestinal mucosa. In a preferred embodiment, chronic gastritis includes chronic atrophic gastritis. In a preferred embodiment, the mucosal damage is gastric mucosal damage caused by an irritant substance or a drug or by a stress state. The irritant substance is, for example, hydrochloric acid, ethanol or alcohol, etc., and the drug is, for example, the non-steroidal anti-inflammatory drug aspirin or indometharin, etc.

Provided is a method for preventing, alleviating or treating a digestive tract disease or eliminating inflammatory edema, the method comprising administering the compound of the present invention or a physiologically compatible salt thereof to a subject. The digestive tract disease includes those associated with oral, esophageal and gastrointestinal diseases, and the oral diseases include oral ulcer, stomatitis, gingivitis, periodontitis, etc.; the esophageal diseases include esophagitis, esophageal ulcer, etc.; and the gastrointestinal diseases include, without limitation, chronic gastritis, chronic atrophic gastritis, acute gastritis, gastroduodenal ulcer, functional gastrointestinal diseases, dyspepsia, precancerous lesions, digestive system tumors, gastrointestinal bleeding, gastroesophageal reflux disease, acute and chronic enteritis, ulcerative colitis, Crohn's disease, and mucosal injuries caused by radiotherapy and/or chemotherapy. In one embodiment, the prevention, alleviation or treatment of digestive tract disease is carried out by regulating the proliferation and differentiation of stem cells. The method can prevent, alleviate or treat a gastrointestinal disease by means of the protective effect of the compound of the present invention or a physiologically compatible salt thereof on digestive tract mucosae such as gastric mucosa or intestinal mucosa or by repairing the injury of digestive tract mucosae such as gastric mucosa or intestinal mucosa.

Provided is a method for repairing a mucosal or skin wound, the method comprising administering the compound of the present invention or a physiologically compatible salt thereof to a subject. In one embodiment, the repair of the mucosal or skin wounds surface includes the regulation of the proliferation and differentiation of stem cells.

In the above method of the present invention, the compound of the present invention or a physiologically compatible salt thereof is administered orally, by injection, subcutaneously, etc.

In a third aspect, provided is a method for repairing skin wound, the method comprising bringing the skin wounds into contact with the compound of the present invention or a physiologically compatible salt thereof. In a preferred embodiment, the skin wounds is related to, but not limited to, epidermal inflammation, mechanical and surgical wound, burns and scalds, ulcers, fistulas, bedsores, and skin injuries caused by radiotherapy and/or chemotherapy. In one embodiment, the skin wounds refers to damage to normal skin caused by external injury-causing factors such as surgery, external forces, heat, electric current, chemicals and low temperatures and internal factors in the body such as local blood supply disturbance. In one embodiment, the skin wounds is often accompanied by the destruction of skin integrity and loss of a certain amount of normal tissues. In another embodiment, the skin wounds include the impairment of the normal function of the skin. In one embodiment, the recovery of the skin wounds is carried out by regulating the proliferation and differentiation of stem cells.

Provided is a method for promoting the proliferation of HaCAT cells, the method comprising bringing the cells into contact with the compound of the present invention or a physiologically compatible salt thereof.

In a fourth aspect, provided is a method for regenerating an injured blood vessel, the method comprising bringing the injured blood vessel into contact with the compound of the present invention or a physiologically compatible salt thereof. In a preferred embodiment, the injured blood vessel includes blood vessel injuries caused by digestive tract mucosa injury and skin wounds.

In a fifth aspect, provided is a pharmaceutical composition, a food composition, a health care or cosmetic composition, or commodity composition, said composition comprising the compound of the present invention or a physiologically compatible salt thereof and a physiologically acceptable carrier. In one embodiment, the physiologically acceptable carrier includes a pharmaceutically acceptable carrier or a cosmetically acceptable carrier. The composition for a medicament, a food product, a health care product or a cosmetic product, or a daily product can be prepared according to a conventional technique of pharmaceutics or cosmetics, including mixing the compound of the present invention, which acts as an active ingredient, with a carrier, and preparing the mixture into the desired dosage form according to a conventional technique. According to requirements, the composition of the present invention can be formulated into an oral preparation, a mucosal preparation, an injection preparation, an inhalation preparation and a topical preparation.

The polypeptide provided has no homology with known polypeptides, which facilitates artificial polypeptide synthesis to obtain a high-purity polypeptide. Compared with epidermal growth factor polypeptides, the polypeptide provided is stable in vivo because it only consists of at most 12 amino acid residues. Moreover, the polypeptide provided can promote the proliferation and differentiation of stem cells, particularly the proliferation and differentiation of gastric organoids, participate in and regulate the proliferation and differentiation of gastric epithelial stem cells, so as to repair the injury of gastrointestinal stem cells and epidermal stem cells, and has the effects of significantly alleviating the pathological development of gastrointestinal diseases such as chronic gastritis and digestive tract ulcers, eliminating inflammatory edema, promoting the repair of digestive tract mucosa injury and skin wound, shortening the wound healing time, modulating immune functions, etc. In addition, the polypeptide provided, when applied to a skin wounds surface of the body surface, can function even after the skin wounds surface is sterilized by an iodine preparation or hydrogen peroxide, or can stably exist even in an artificial gastric juice, an artificial intestinal juice, etc., whereas the epidermal growth factor, when applied to the skin of the body surface, will be structurally destroyed and cannot function after disinfection with an iodine preparation or hydrogen peroxide.

DETAILED DESCRIPTION OF EMBODIMENTS

The term "physiologically compatible salt" refers to a salt form that is physiologically compatible (i.e., pharmacologically acceptable) and substantially non-toxic to an individual to whom the compound of the present invention is to be administered. Physiologically compatible salts of the compound of the present invention include conventional and stoichiometric acid addition salts or base addition salts formed from suitable, non-toxic organic or inorganic acids or inorganic bases.

The term "subject" refers to an animal, preferably a mammal, most preferably a human. Specifically, the term "subject" relates to a mammal or human with skin wounds and/or mucosal damage. It should be understood by those skilled in the art that the repair of skin wounds and/or mucosal damage in the present invention can be applied for cosmetic purposes (i.e., non-therapeutic purposes) and therapeutic purposes. To this end, the term "skin injury" in the present application further includes skin injuries to be repaired for cosmetic purposes, such as wrinkles (e.g., wrinkles caused by ultraviolet radiation), skin lines, cracks, lumps, large pores (e.g., those related to accessory structures such as sweat ducts, sebaceous glands or hair follicles), or unevenness or roughness, loss of skin elasticity (loss and/or inactivation of functional skin elastin), sagging (including dropsy of eyes and jaw), loss of skin hardness, loss of skin firmness, loss of recovery ability after skin deformation, discoloration (including dark circles under eyes), macula and blisters, sallow complexion, hyperpigmented skin areas such as senile plaques and freckles, cutin, abnormal differentiation, excessive keratinization, degenerated elastic tissues, destructed collagen, and other tissue changes in skin keratin, dermis, epidermis, skin vascular systems (such as telangiectasia or multi-branched blood vessels) and subcutaneous tissues, especially those close to the skin.

The following is a description of the present invention in conjunction with specific trials and is not a limitation on the scope of protection of the present invention.

TABLE 1

English names or abbreviations of reagents and solvents used in writing

| English name or abbreviation | Chinese name |
|---|---|
| HBTU | Benzotriazole-N,N,N',N'-tetramethyluronium hexafluorophosphate |
| Methanol | Methanol |
| Tert-Butyl methyl ether | Tert-Butyl methyl ether |
| Ethanol | Ethanol |
| AA | Amino acid |

Example 1: Chemical Synthesis of Polypeptide

A polypeptide compound was synthesized by a conventional solid-phase synthesis method via multiple cyclic processes of resin swelling, substitution, deprotection, washing, amino acid dissolution, amino acid activation and condensation processes, washing, and further deprotection, and finally cleavage and side chain deprotection.

Figure 1:
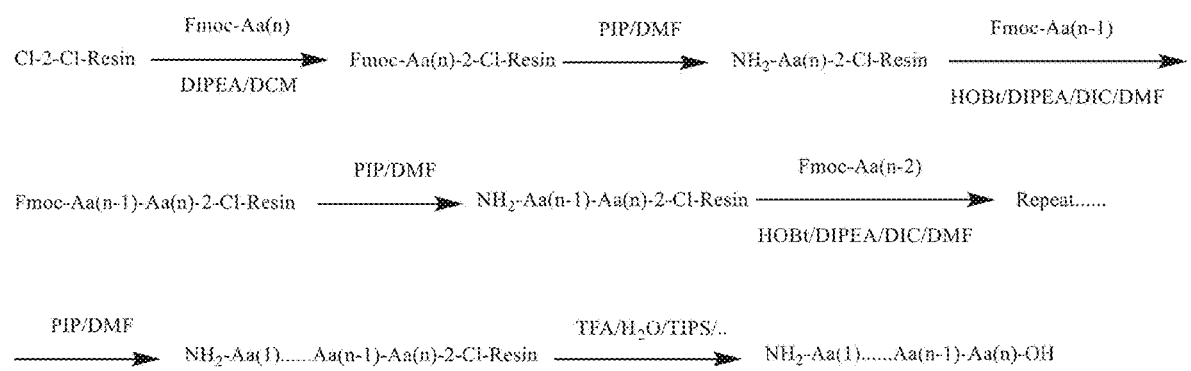
FIG. 1 shows a schematic diagram of the steps of the solid-phase synthesis of a polypeptide.

The schematic diagram of the steps of the solid-phase synthesis of the polypeptide was shown in FIG. 1. In FIG. 1, Cl-2-Cl-Resin represented 2-chlorotrityl chloride resin; Fmoc-Aa (n) represented an amino acid with 9-fluorenyl-methoxycarbonyl; DIPEA was N,N-diisopropylethylamine; DCM was dichloromethane; PIP was piperidine; DMF was N,N-dimethylformamide; HOBt was 1-hydroxybenzotriazole; DIC was N,N'-diisopropyl carbodiimide; TFA was trifluoroacetic acid; and TIPS was triisopropylsilane.

Hereinafter, taking the compound of SEQ ID NO: 1 (Pro-Ala-Ala-Glu-Pro-Val-Pro-Leu-Val-Lys-Gln-Asp) as an example, a method for the synthesis and purification of the compound of SEQ ID NO: 1 was shown, the method comprising step 1. preparation of fully protected peptide resin; 2. cutting and deprotection; and 3. purification (salt exchange) and freeze-drying.

1. Preparation of Fully Protected Peptide Resin (1) Resin swelling: 2.0192 g of 2-Chlorotrityl Chloride Resin (S=0.73 mmol/g) was weighed, added to a synthesis tube with a sieve plate, swelled with 40 ml of dichloromethane for 30 min, and subjected to suction filtration to remove dichloromethane.

(2) Preparation of Fmoc-Asp (OtBu)-Resin: Based on a molar ratio of 1:1.5:1.65 of resin to Fmoc-Asp (OtBu)-OH to DIPEA, Fmoc-Asp (OtBu)-OH and DIPEA were respectively weighed, dissolved in 20 ml of dichloromethane and added to the synthesis tube. Bubbling with $N_2$ and shaking were performed at room temperature for 1-3 hours, and 2 ml of methanol was directly added to the reaction solution, followed by blocking for 30 min. It was then washed 4 times separately with dimethylformamide, 25 ml each time, and the resin was dried by draining.

(3) Removal of Fmoc protecting group: 20 ml of a 20% piperidine-DMF (v/v) solution was added to the reactor, the reaction was bubbled with $N_2$ for 20 min, and draining was performed; and it was then washed with dimethylformamide 6 times, 25 ml each time, 3 min each time, and after draining, the results of Fmoc removal were detected by ninhydrin method.

(4) Amino acid pre-activation: 4.38 mmol of Fmoc-protected amino acid, 5.26 mmol of HOBt, 4.60 mmol of DIC were added to a 250 ml round bottom flask, dissolved in 20 ml of 1:1 DCM-DMF (v/v), and pre-activated in an ice bath at −5° C. to 0° C. under stirring for 30-60 min.

(5) Amino acid connection: the activated protected amino acid solution was poured into the reactor, and an appropriate amount of DCM was supplemented to clean the tools. After the reaction was bubbled with $N_2$ at room temperature for 1-3 hours, ninhydrin method was used to detect whether the amino acid connection was complete and if so, draining was performed. The resin was washed with dimethylformamide 4 times, 25 ml each time, 3 min each time, and draining was performed. The amount of each amino acid and condensing agent and the specific reaction time were shown in Table 2.

(6) After the condensation of the first amino acid was complete, steps (3) to (5) were repeated to extend the peptide chain according to the amino acid sequence until the coupling of the last amino acid was completed.

(7) The resin peptide was washed with dichloromethane 6 times, 25 ml each time, 3 min each time, and draining was performed.

TABLE 2

Amounts of amino acids and condensing agent

| Amino acid name | AA/eq | Amino acid amount/g | HOBt/g | DIPEA/g | DIC/g |
|---|---|---|---|---|---|
| Fmoc-L-Asp(OtBu)—OH | 2.19 | 0.90 | 0 | 0.31 | 0 |
| Fmoc-L-Gln(Trt)-OH | 4.38 | 2.67 | 0.71 | 0.57 | 0.58 |
| Fmoc-L-Lys(Boc)-OH | 4.38 | 2.05 | 0.71 | 0.57 | 0.58 |
| Fmoc-L-Val-OH | 4.38 | 1.49 | 0.71 | 0.57 | 0.58 |
| Fmoc-L-Leu-OH | 4.38 | 1.55 | 0.71 | 0.57 | 0.58 |
| Fmoc-L-Pro-OH | 4.38 | 1.48 | 0.71 | 0.57 | 1.16 |
| Fmoc-L-Val-OH | 4.38 | 1.49 | 0.71 | 0.57 | 0.58 |
| Fmoc-L-Pro-OH | 4.38 | 1.48 | 0.71 | 0.57 | 1.16 |
| Fmoc-L-Glu(OtBu)—OH•H$_2$O | 4.38 | 1.94 | 0.71 | 0.57 | 1.16 |
| Fmoc-L-Ala-OH•H$_2$O | 4.38 | 1.44 | 0.71 | 0.57 | 1.16 |
| Fmoc-L-Ala-OH•H$_2$O | 4.38 | 1.44 | 0.71 | 0.57 | 1.16 |
| Fmoc-L-Pro-OH | 4.38 | 1.48 | 0.71 | 0.57 | 1.16 |

Step 2. Cleavage and Deprotection (1) 50 ml of a cleaving agent (TFA: TIPS: H2O =95:2.5: 2.5, v/v) was added to the synthesis tube in step 1, and the reaction was bubbled with N$_2$ for 1.5-3 hours.

(2) After the cleavage reaction was complete, the cleavage agent was suction-filtered into a 250 ml round bottom flask. After vacuum concentration to one third of the original volume of the cleavage agent, add 10 folds of the existing volume of methyl tert-butyl ether was added, and the mixture was stirred for 30 min. The resulting mixed solvent was filtered and washed three times separately with 30 ml of methyl tert-butyl ether, and the resulting crude peptide product was put into a sand core funnel and dried with N$_2$ in a fume hood, so that the solvent was volatilized until the crude peptide became powder. The obtained crude peptide was 1.87 g and had a crude yield of 85.1%.

Step 3. Purification (Salt Exchange) and Freeze-Drying

Using the following chromatographic parameter condition A, the crude peptide obtained in step 2 was purified by HPLC. Specifically, the crude peptide obtained in step 2 was dissolved with water and/or acetonitrile, and filtered by a 0.45 μm filter membrane; sample injection was performed; gradient elution was performed with an acetonitrile-water mobile phase; a peptide eluent of interest was collected; and finally, rotary evaporation concentration was performed.

Chromatographic parameter condition A:

Chromatographic column: YMC-Actus Triart C18 30*250 mm;

Eluent A: 0.1% (v/v) TFA/H$_2$O;

Eluent B: acetonitrile;

Flow rate: 25 ml/min;

Ultraviolet detection wavelength: 220 nm;

TABLE 3

Gradient elution conditions

| Time, min | Eluent A (%) | Eluent B (%) |
|---|---|---|
| 0 | 90 | 10 |
| 30 | 75 | 25 |

Next, the product obtained in the previous step was subjected to salt exchange by HPLC method using the following chromatographic parameter condition B, whereby the final peptide the compound of SEQ ID NO: 1 was obtained. Specifically, 95% A1+5% B balanced chromatographic column was used; sample injection was then performed; next, 95% A2+5% B balanced chromatographic column was used; gradient elution was performed with A1 and B; a peptide eluent of interest was collected; and finally, rotary evaporation concentration and freeze-drying were performed to obtain the compound of SEQ ID NO: 1 (purification yield 73.3%, purity 100%). The structure of the compound of SEQ ID NO: 1 was confirmed by MS and $^1$H-NMR.

Chromatographic parameter condition B:

Chromatographic column: YMC-Actus Triart C18 30*250 mm

Eluent A1: 0.1 M acetic acid

Eluent A2: 0.025 M acetic acid+0.1 M ammonium acetate

Eluent B: acetonitrile

Flow rate: 25 ml/min

Ultraviolet detection wavelength: 220 nm

TABLE 4

Gradient elution conditions

| Time, min | Eluent A1 (%) | Eluent B (%) |
|---|---|---|
| 0 | 95 | 5 |
| 5 | 95 | 5 |
| 35 | 70 | 30 |

Other compounds were synthesized in a similar way to the synthesis of the compound of SEQ ID NO: 1. The results were shown in Table 5 and the other parts of the description.

TABLE 5

| | | | Synthesized compounds | | |
|---|---|---|---|---|---|
| SEQ ID NO: | Compound sequence | Amount of crude product (g) | Yield (after purification) | Purity | MS |
| 1 | Pro-Ala-Ala-Glu-Pro-Val-Pro-Leu-Val-Lys-Gln-Asp | 1.87 | 73.3% | 100% | 1263.70, 632.50 (double charge), and 422.10 (triple charge) |
| 2 | Gly-Ala-Ala-Glu-Pro-Val-Pro-Leu-Val-Lys-Gln-Asp | 2.07 | N/A | 100.0% | 612.60 (double charge) |
| 3 | Pro-Ala-Ala-Glu-Pro-Val-Pro-Leu-Val-Lys | 1.62 | 33.8% | 99.8% | 511.00 (double charge) |
| 4 | Pro-Ala-Ala-Glu-Gly-Val-Pro-Leu-Val-Lys-Gln-Asp | 2.00 | 56.8% | 97.9% | 612.60 (double charge) |
| 5 | Pro-Ala-Ala-Glu-Pro-Val-Gly-Leu-Val-Lys-Gln-Asp | 1.50 | 42.3% | 99.2% | 612.50 (double charge) |
| 6 | Pro-Ala-Ala-Glu-Pro-Val-Gly-Ala-Val-Lys-Gln-Asp | 1.78 | 38.1% | 100.0% | 591.50 (double charge) |
| 7 | Pro-Ala-Ala-Glu-Pro-Val-Gly-Val-Val-Lys-Gln-Asp | 1.50 | 46.5% | 100.0% | 605.50 (double charge) |
| 8 | Pro-Ala-Ala-Glu-Gly-Val-Gly-Leu-Val-Lys-Gln-Asp | 2.15 | 14.4% | 100.0% | 592.50 (double charge) |
| 9 | Pro-Ala-Ala-Glu-Gly-Val-Gly-Leu | 2.12 | 67.9% | 98.9% | 713.40 |
| 10 | Pro-Ala-Ala-Gln-Pro-Val-Pro-Leu-Val-Lys-Gln-Asp | 2.36 | 57.4% | 100.0% | 632.00 (double charge) |
| 11 | Pro-Ala-Ala-Asp-Pro-Val-Pro-Leu-Val-Lys-Gln-Asp | 2.39 | 52.9% | 99.6% | 625.50 (double charge) |
| 12 | Pro-Ala-Ala-Glu-Pro-Val-Pro-Phe-Val-Lys-Gln-Asp | 2.95 | 78.3% | 100.0% | 649.5 (double charge) and 433.4 (triple charge) |
| 13 | Pro-Ala-Ala-Glu-Pro-Val-Pro-Tyr-Val-Lys-Gln-Asp | 2.66 | 38.4% | 100.0% | 657.4 (double charge) and 438.8 (triple charge) |
| 14 | Pro-Ala-Ala-Glu-Pro-Val-Gly-Leu-Val-Lys | 1.92 | 53.5% | 100.0% | 490.9 (double charge) |
| 15 | Pro-Ala-Ala-Glu-Pro-Val-Gly-Val-Val-Lys | 1.81 | 56.9% | 100.0% | 483.8 (double charge) |
| 16 | Pro-Ala-Ala-Glu-Pro-Val-Ala-Leu-Val-Lys | 1.98 | 60.1% | 100.0% | 497.8 (double charge) |
| 17 | Pro-Ala-Ala-Glu-Pro-Val-Ala-Val-Val-Lys | 2.04 | 57.3% | 100.0% | 490.9 (double charge) |
| 18 | Pro-Ala-Ala-Glu-Ala-Val-Pro-Leu-Val-Lys-Gln-Asp | 2.15 | 52.0% | 100.0% | 619.5 (double charge) |
| 19 | Pro-Ala-Ala-Glu-Pro-Val-Ala-Leu-Val-Lys-Gln-Asp | 1.92 | 37.7% | 100.0% | 619.4 (double charge) |
| 20 | Pro-Ala-Ala-Glu-Ala-Val-Ala-Leu-Val-Lys-Gln-Asp | 1.96 | 19.1% | 99.7% | 606.50 (double charge) |
| 21 | Ala-Ala-Ala-Glu-Pro-Val-Pro-Leu-Val-Lys-Gln-Asp | 2.58 | 61.6% | 100.0% | 619.50 (double charge) |
| 22 | Pro-Ala-Ala-Glu-Pro-Val-Pro-Phe-Val-Lys | 2.11 | 53.8% | 100.0% | 527.8 (double charge) |
| 23 | Pro-Ala-Ala-Glu-Pro-Val-Pro-Tyr-Val-Lys | 2.05 | 51.1% | 100.0% | 535.8 (double charge) |

TABLE 5-continued

Synthesized compounds

| SEQ ID NO: | Compound sequence | Amount of crude product (g) | Yield (after purification) | Purity | MS |
|---|---|---|---|---|---|
| 24 | Pro-Ala-Ala-Glu-Pro-Val-Gly-Phe-Val-Lys | 1.81 | 55.5% | 100.0% | 507.9 (double charge) |
| 25 | Pro-Ala-Ala-Glu-Pro-Val-Ala-Phe-Val-Lys | 1.81 | 59.0% | 100.0% | 514.8 (double charge) |
| 26 | Pro-Ala-Ala-Glu-Pro-Val-Pro-Leu | 1.57 | 60.3% | 100.0% | 793.4 and 397.3 (double charge) |
| 27 | Ala-Glu-Pro-Val-Pro-Leu-Val-Lys-Gln-Asp | 2.52 | 48.3% | 100.0% | 548.5 (double charge) |
| 28 | Pro-Val-Pro-Leu-Val-Lys-Gln-Asp | 2.05 | 43.6% | 100.0% | 448.40 (double charge) |
| 29 | Pro-Ala-Ala-Glu-Pro-Val-Pro | 1.62 | 55.4% | 100.0% | 680.40 |
| 30 | Ala-Glu-Pro-Val-Pro-Leu | 2.70 | 71.7% | 100.0% | 625.10 |
| 31 | Glu-Pro-Val-Pro-Leu | 1.82 | 52.2% | 97.9% | 554.40 |
| 32 | Pro-Val-Pro-Leu | N/A | 46.4% | 100.0% | 425.30 |
| 33 | Ala-Ala-Glu-Pro-Val-Pro-Leu | 3.02 | 60.3% | 100.0% | 696.40 |
| 34 | Pro-Ala-Ala-Glu-Pro-Val | 2.50 | 94.3% | 100.0% | 583.40 |
| 35 | Pro-Ala-Ala-Glu-Pro | 2.05 | 59.3% | 99.2% | 484.30 |
| 36 | Pro-Ala-Ala-Glu | 2.53 | 65.3% | 100.0% | 387.30 |
| 37 | Ala-Ala-Glu-Pro-Val-Pro-Leu-Val-Lys-Gln-Asp | 2.54 | N/A | 100.0% | 584.10 (double charge) |
| 38 | Glu-Pro-Val-Pro-Leu-Val-Lys-Gln-Asp | 2.48 | 56.0% | 94.1% | 513.00 (double charge) |
| 39 | Val-Pro-Leu-Val-Lys-Gln-Asp | 1.95 | 57.9% | 100.0% | 399.90 (double charge) |
| 40 | Pro-Leu-Val-Lys-Gln-Asp | 1.82 | 49.8% | 100.0% | 350.30 (double charge) |
| 41 | Pro-Ala-Ala-Glu-Pro-Val-Pro-Ile-Val-Lys | 2.04 | 58.5% | 99.6% | 511.00 (double charge) |
| 42 | Pro-Ala-Ala-Glu-Pro-Val-Pro-Val-Val-Lys | 2.22 | 56.7% | 98.7% | 504.00 (double charge) |
| 43 | Pro-Ala-Ala-Glu-Pro-Val-Pro-Met-Val-Lys | 2.22 | 48.8% | 98.6% | 520.10 (double charge) |
| 44 | Ala-Glu-Pro-Val-Pro | 2.37 | 47.8% | 100.0% | 512.40 |
| 45 | Ala-Glu-Pro-Val | 0.43 | 57.8% | 100.0% | 415.30 |
| 46 | Pro-Ala-Ala-Asn-Pro-Val-Pro-Leu-Val-Lys-Gln-Asp | 2.58 | 57.5% | 100.0% | 625.10 (double charge) |
| 47 | Pro-Ala-Ala-Leu-Pro-Val-Pro-Leu-Val-Lys-Gln-Asp | 2.68 | 57.9% | 100.0% | 624.50 (double charge) |
| 48 | Pro-Ala-Gly-Glu-Pro-Val-Pro-Leu-Val-Lys-Gln-Asp | 2.74 | 56.7% | 100.0% | 625.50 (double charge) |
| 49 | Pro-Ala-Pro-Glu-Pro-Val-Pro-Leu-Val-Lys-Gln-Asp | 2.92 | 22.2% | 100.0% | 645.40 (double charge) |
| 50 | Pro-Ala-Ala-Glu-Pro-Val-Pro-Leu-Val-Lys-Gln-Asn | 3.10 | 48.4% | 100.0% | 632.10 (double charge) |
| 51 | Pro-Ala-Ala-Glu-Pro-Val-Pro-Leu-Val-Val-Gln-Asp | 2.71 | 53.9% | 100.0% | 618.00 (double charge) |

TABLE 5-continued

Synthesized compounds

| SEQ ID NO: | Compound sequence | Amount of crude product (g) | Yield (after purification) | Purity | MS |
|---|---|---|---|---|---|
| 52 | Pro-Ala-Ala-Glu-Pro-Val-Pro-Val-Val-Lys-Gln-Asp | 3.13 | 57.1% | 100.0% | 625.60 (double charge) |
| 53 | Pro-Ala-Ala-Glu-Pro-Val-Pro-Ile-Val-Lys-Gln-Asp | 3.25 | 53.5% | 100.0% | 632.60 (double charge) |
| 54 | Pro-Ala-Ala-Glu-Pro-Val-Pro-Met-Val-Lys-Gln-Asp | 1.82 | 59.4% | 100.0% | 641.60 (double charge) |
| 55 | Pro-Leu-Ala-Glu-Pro-Val-Pro-Leu-Val-Lys-Gln-Asp | 2.34 | 62.7% | 100.0% | 653.60 (double charge) |
| 56 | Pro-Ile-Ala-Glu-Pro-Val-Pro-Leu-Val-Lys-Gln-Asp | 3.22 | 41.9% | 100.0% | 653.60 (double charge) |
| 57 | Pro-Ala-Ala-Glu-Pro-Val-Pro-Leu-Val-Lys-Glu-Asp | 2.38 | 61.3% | 100.0% | 633.10 (double charge) |
| 58 | Pro-Ala-Ala-Glu-Pro-Val-Pro-Leu-Val-Lys-Asn-Asp | 3.10 | 57.7% | 100.0% | 625.60 (double charge) |
| 59 | Pro-Ala-Ala-Glu-Pro-Val-Pro-Leu-Val-Lys-Asp-Asp | 2.66 | 51.7% | 99.5% | 626.10 (double charge) |
| 60 | Pro-Ala-Ala-Glu-Pro-Val-Pro-Leu-Val-Lys-Gln-Glu | 1.91 | 80.8% | 99.5% | 639.60 (double charge) |
| 61 | Pro-Ala-Leu-Glu-Pro-Val-Pro-Leu-Val-Lys-Gln-Asp | 2.14 | 64.7% | 100.0% | 653.60 (double charge) |
| 62 | Pro-Ala-Ile-Glu-Pro-Val-Pro-Leu-Val-Lys-Gln-Asp | 1.93 | 72.1% | 100.0% | 653.60 (double charge) |
| 63 | Pro-Ala-Ala-Glu-Pro-Val-Pro-Leu-Leu-Lys-Gln-Asp | 2.21 | 61.8% | 100.0% | 639.60 (double charge) |
| 64 | Pro-Ala-Ala-Glu-Pro-Val-Pro-Leu-Ile-Lys-Gln-Asp | 2.53 | 57.2% | 100.0% | 639.60 (double charge) |
| 65 | Pro-Ala-Ala-Glu-Pro-Val-Pro-Leu-Met-Lys-Gln-Asp | 3.17 | 33.3% | 100.0% | 648.50 (double charge) |
| 66 | Pro-Ala-Ala-Glu-Pro-Val-Pro-Leu-Val-Arg-Gln-Asp | 1.35 | 49.8% | 100.0% | 646.60 (double charge) |
| 67 | Pro-Ala-Ala-Val-Pro-Val-Pro-Leu-Val-Lys-Gln-Asp | 2.24 | 54.4% | 100.0% | 617.60 (double charge) |
| 68 | Val-Pro-Leu-Val-Lys-Gln-Asp | 1.68 | 53.3% | 100.0% | 399.90 (double charge) |
| 69 | Gly-Ala-Ala-Val-Pro-Val-Pro-Leu-Val-Lys-Gln-Asp | 1.66 | 58.9% | 100.0% | 597.60 (double charge) |
| 70 | Gly-Ala-Gly-Val-Pro-Val-Pro-Leu-Val-Lys-Gln-Asp | 2.42 | 45.0% | 100.0% | 590.60 (double charge) |
| 71 | Gly-Ala-Gly-Val-Gly-Val-Pro-Leu-Val-Lys-Gln-Asp | 1.94 | 54.5% | 100.0% | 570.50 (double charge) |
| 72 | Pro-Ala-Ala-Glu-Pro-Val-Ala-Phe-Val-Lys-Gln-Asp | 3.20 | 43.3% | 100.0% | 636.60 (double charge) |
| 73 | Val-Pro-Leu-Val | 2.37 | 58.3% | 100.0% | 427.40 |

Note:
Double charge represented 1/2 target peak in the mass spectrum, and triple charge represented 1/3 target peak in the mass spectrum; N/A represented having difficulties in weighing, and no actual weight was considered.

SEQ ID NO: 1: Pro-Ala-Ala-Glu-Pro-Val-Pro-Leu-Val-Lys-Gln-Asp acetate
$^1$H NMR (600 MHZ, DMSO) δ 8.27 (d, J=7.6 Hz, 1H), 8.21 (d, J=7.8 Hz, 1H), 8.09 (d, J=7.5 Hz, 1H), 8.03 (d, J=7.9 Hz, 1H), 7.99 (d, J=7.4 Hz, 1H), 7.94 (dd, J=16.7, 8.0 Hz, 2H), 7.58 (d, J=6.3 Hz, 1H), 7.51 (d, J=8.6 Hz, 1H), 7.16 (s, 1H), 6.70 (s, 1H), 4.48 (dd, J=13.3, 7.9 Hz, 1H), 4.39 (dd, J=8.2, 4.2 Hz, 1H), 4.35-4.21 (m, 6H), 4.18-4.03 (m, 3H), 3.71-3.47 (m, 5H), 2.93-2.69 (m, 4H), 2.45-2.32 (m, 2H), 2.25 (t, J=7.7 Hz, 2H), 2.08 (t, J=7.9 Hz, 2H), 2.01-1.93 (m, 3H), 1.93-1.84 (m, 14H, AcOH), 1.84-1.76 (m, 3H), 1.75-1.57 (m, 8H), 1.54-1.39 (m, 5H), 1.36-1.27 (m, 2H), 1.21-1.10 (m, 6H), 0.91-0.74 (m, 18H).

SEQ ID NO: 3: Pro-Ala-Ala-Glu-Pro-Val-Pro-Leu-Val-Lys acetate $^1$H NMR (600 MHz, DMSO) δ 8.22-8.13 (m, 2H), 8.10 (s, 1H), 7.98 (d, J=7.6 Hz, 1H), 7.92 (d, J=8.4 Hz, 1H), 7.72 (s, 1H), 7.59 (s, 1H), 4.52-4.43 (m, 1H), 4.39-4.19 (m, 6H), 4.12-4.04 (m, 1H), 3.89 (d, J=5.9 Hz, 1H), 3.67-3.46 (m, 6H), 2.85 (dt, J=10.2, 6.8 Hz, 1H), 2.80-2.73 (m, 1H), 2.69 (s, 2H), 2.21 (t, J=7.4 Hz, 2H), 2.03-1.76 (m, 14H, AcOH), 1.73 (d, J=5.5 Hz, 1H), 1.70-1.61 (m, 4H), 1.61-1.52 (m, 3H), 1.47 (s, 4H), 1.26 (s, 2H), 1.20-1.12 (m, 6H), 0.91-0.83 (m, 9H), 0.83-0.77 (m, 9H).

SEQ ID NO: 4: Pro-Ala-Ala-Glu-Gly-Val-Pro-Leu-Val-Lys-Gln-Asp acetate $^1$H NMR (600 MHZ, D$_2$O) δ 4.45-4.16 (m, 10H), 4.04 (d, J=8.1 Hz, 1H), 3.93-3.76 (m, 3H), 3.67-3.58 (m, 1H), 3.42-3.28 (m, 2H), 2.94 (t, J=7.4 Hz, 2H), 2.72 (qd, J=16.4, 6.0 Hz, 2H), 2.45-2.27 (m, 5H), 2.27-2.16 (m, 1H), 2.11-1.86 (m, 17H, AcOH), 1.84-1.47 (m, 8H), 1.45-1.25 (m, 8H), 0.91 (d, J=6.8 Hz, 3H), 0.89-0.73 (m, 15H).

SEQ ID NO: 5: Pro-Ala-Ala-Glu-Pro-Val-Gly-Leu-Val-Lys-Gln-Asp acetate $^1$H NMR (600 MHZ, D$_2$O+D$_3$COD) δ 4.66-4.62 (m, 2H), 4.40 (dd, J=8.1, 5.9 Hz, 1H), 4.35-4.21 (m, 6H), 4.03-3.98 (m, 2H), 3.92-3.81 (m, 3H), 3.78-3.71 (m, 1H), 3.62 (dt, J=10.3, 7.1 Hz, 1H), 3.39-3.30 (m, 2H), 2.96-2.87 (m, 4H), 2.51-2.35 (m, 3H), 2.32 (t, J=7.6 Hz, 2H), 2.26-2.19 (m, 1H), 2.10-1.91 (m, 14H, AcOH), 1.91-1.78 (m, 2H), 1.78-1.71 (m, 1H), 1.70-1.58 (m, 3H), 1.53 (d, J=3.6 Hz, 3H), 1.42-1.34 (m, 2H), 1.33 (d, J=7.2 Hz, 3H), 1.30 (d, J=7.2 Hz, 3H), 0.94-0.88 (m, 6H), 0.88-0.83 (m, 9H), 0.82-0.79 (m, 3H).

SEQ ID NO: 8: Pro-Ala-Ala-Glu-Gly-Val-Gly-Leu-Val-Lys-Gln-Asp acetate $^1$H NMR (600 MHZ, DMSO) δ 8.30-8.24 (m, 3H), 8.15 (d, J=7.3 Hz, 1H), 8.11-8.03 (m, 2H), 7.94 (d, J=7.4 Hz, 1H), 7.88 (d, J=8.0 Hz, 1H), 7.80 (t, J=9.4 Hz, 2H), 7.59 (d, J=6.4 Hz, 1H), 7.17 (s, 1H), 6.70 (s, 1H), 4.44-3.99 (m, 10H), 3.82-3.57 (m, 7H), 2.94-2.69 (m, 5H), 2.47-2.41 (m, 1H), 2.41-2.32 (m, 1H), 2.21 (t, J=7.9 Hz, 2H), 2.08 (t, J=7.9 Hz, 2H), 2.03-1.79 (m, 11H, AcOH), 1.78-1.26 (m, 14H), 1.19 (dd, J=6.9, 4.7 Hz, 6H), 0.87-0.76 (m, 18H).

SEQ ID NO: 9: Pro-Ala-Ala-Glu-Gly-Val-Gly-Leu $^1$H NMR (600 MHZ, DMSO) δ 8.43 (d, J=7.6 Hz, 1H), 8.29-8.23 (m, 2H), 8.22-8.14 (m, 2H), 7.81 (d, J=8.5 Hz, 1H), 7.75 (d, J=7.9 Hz, 1H), 4.32-4.08 (m, 5H), 3.78-3.69 (m, 4H), 3.63 (dd, J=16.4, 5.6 Hz, 1H), 2.98-2.86 (m, 2H), 2.22 (t, J=7.9 Hz, 2H), 2.07-1.92 (m, 2H), 1.92-1.86 (m, 1H), 1.79-1.64 (m, 4H), 1.62-1.54 (m, 1H), 1.50-1.40 (m, 2H), 1.19 (dd, J=7.0, 1.3 Hz, 6H), 0.86-0.78 (m, 12H).

SEQ ID NO: 10: Pro-Ala-Ala-Gln-Pro-Val-Pro-Leu-Val-Lys-Gln-Asp acetate $^1$H NMR (600 MHz, DMSO) δ 8.28 (d, J=7.7 Hz, 1H), 8.14 (d, J=7.8 Hz, 1H), 8.07 (d, J=7.4 Hz, 1H), 8.04 (d, J=8.0 Hz, 1H), 8.00 (d, J=7.3 Hz, 1H), 7.95 (t, J=15.3 Hz, 2H), 6.76 (s, 1H), 6.70 (s, 1H), 4.45 (q, J=13.6, 7.9 Hz, 1H), 4.39 (dd, J=8.3, 4.1 Hz, 1H), 4.33-4.20 (m, 6H), 4.20-4.09 (m, 2H), 4.09-4.02 (m, 1H), 3.69-3.47 (m, 5H), 2.86 (dt, J=10.2, 6.7 Hz, 1H), 2.80-2.62 (m, 3H), 2.46-2.40 (m, 1H), 2.37 (dd, J=15.5, 2.7 Hz, 1H), 2.14-2.03 (m, 4H), 2.02-1.76 (m, 16H, AcOH), 1.75-1.39 (m, 13H), 1.39-1.22 (m, 2H), 1.22-1.11 (m, 6H), 1.00-0.68 (m, 18H).

SEQ ID NO: 11: Pro-Ala-Ala-Asp-Pro-Val-Pro-Leu-Val-Lys-Gln-Asp acetate $^1$H NMR (600 MHZ, DMSO) δ 8.26 (d, J=7.6 Hz, 1H), 8.19 (d, J=7.7 Hz, 1H), 8.09 (d, J=7.7 Hz, 1H), 8.04 (d, J=7.5 Hz, 1H), 7.96 (t, J=7.4 Hz, 2H), 7.87 (d, J=7.0 Hz, 1H), 7.60 (d, J=6.4 Hz, 1H), 7.37 (d, J=8.9 Hz, 1H), 7.17 (s, 1H), 6.70 (s, 1H), 4.70 (q, J=14.2, 7.0 Hz, 1H), 4.37-4.21 (m, 7H), 4.16-4.10 (m, 2H), 4.09-4.03 (m, 1H), 3.74-3.67 (m, 2H), 3.68-3.59 (m, 4H), 3.49-3.45 (m, 1H), 2.99-2.84 (m, 3H), 2.80-2.71 (m, 2H), 2.63 (dd, J=16.5, 7.5 Hz, 1H), 2.46-2.25 (m, 4H), 2.07 (t, J=7.9 Hz, 2H), 2.05-1.76 (m, 20H, AcOH), 1.74-1.58 (m, 6H), 1.56-1.42 (m, 5H), 1.32 (d, J=8.0 Hz, 2H), 1.18 (d, J=7.0 Hz, 3H), 1.14 (d, J=7.1 Hz, 3H), 0.88-0.74 (m, 18H).

SEQ ID NO: 12: Pro-Ala-Ala-Glu-Pro-Val-Pro-Phe-Val-Lys-Gln-Asp acetate $^1$H NMR (600 MHZ, DMSO) δ 8.29 (d, J=7.5 Hz, 1H), 8.17 (d, J=7.7 Hz, 1H), 8.09 (d, J=7.4 Hz, 1H), 8.03 (d, J=7.2 Hz, 1H), 7.96 (d, J=7.6 Hz, 1H), 7.90 (d, J=8.7 Hz, 1H), 7.86 (d, J=7.9 Hz, 1H), 7.73 (d, J=8.5 Hz, 1H), 7.58 (d, J=6.4 Hz, 1H), 7.25-7.19 (m, 4H), 7.18-7.12 (m, 2H), 6.71 (s, 1H), 4.54-4.44 (m, 1H), 4.37 (q, J=8.3 Hz, 1H), 4.33-4.21 (m, 5H), 4.19-4.10 (m, 2H), 4.09-4.02 (m, 1H), 3.64-3.53 (m, 5H), 3.51-3.45 (m, 2H), 3.00 (dd, J=9.6 Hz, 1H), 2.89-2.82 (m, 2H), 2.80-2.71 (m, 3H), 2.46-2.36 (m, 2H), 2.24 (t, J=7.4 Hz, 2H), 2.08 (t, J=8.0 Hz, 2H), 2.00-1.70 (m, 18H, AcOH), 1.69-1.64 (m, 2H), 1.63-1.56 (m, 2H), 1.55-1.47 (m, 3H), 1.34 (s, 2H), 1.16 (t, J=6.9 Hz, 6H), 0.87-0.76 (m, 12H).

SEQ ID NO: 26: Pro-Ala-Ala-Glu-Pro-Val-Pro-Leu acetate $^1$H NMR (600 MHZ, DMSO) δ 8.25 (s, 1H), 8.09 (d, J=7.5 Hz, 1H), 7.94 (d, J=7.6 Hz, 1H), 7.89 (d, J=8.3 Hz, 2H), 4.53-4.46 (m, 1H), 4.39 (dd, J=8.3, 4.2 Hz, 1H), 4.34 (dd, J=8.4, 3.8 Hz, 1H), 4.31-4.19 (m, 3H), 4.13 (dd, J=15.1, 7.7 Hz, 1H), 3.71-3.49 (m, 5H), 2.94-2.77 (m, 2H), 2.33-2.20 (m, 2H), 2.06-1.77 (m, 13H, AcOH), 1.77-1.56 (m, 6H), 1.46 (t, J=7.3 Hz, 2H), 1.25-1.11 (m, 6H), 0.95-0.76 (m, 12H).

SEQ ID NO: 27: Ala-Glu-Pro-Val-Pro-Leu-Val-Lys-Gln-Asp acetate $^1$H NMR (600 MHZ, D$_2$O) δ 4.61 (dd, J=9.6, 4.4 Hz, 1H), 4.44-4.22 (m, 8H), 4.09-3.99 (m, 2H), 3.85-3.72 (m, 2H), 3.69-3.57 (m, 2H), 2.94 (t, J=7.4 Hz, 2H), 2.79-2.63 (m, 2H), 2.43-2.16 (m, 7H), 2.09-1.74 (m, 19H, AcOH), 1.73-1.47 (m, 7H), 1.48-1.13 (m, 6H), 1.00-0.79 (m, 21H).

SEQ ID NO: 28: Pro-Val-Pro-Leu-Val-Lys-Gln-Asp acetate $^1$H NMR (600 MHZ, DMSO) δ8.28 (d, J=7.8 Hz, 1H), 8.13-7.87 (m, 3H), 7.57 (d, J=6.4 Hz, 1H), 7.50 (d, J=8.7 Hz, 1H), 7.15 (s, 1H), 6.69 (s, 1H), 4.40-4.31 (m, 2H), 4.29-4.21 (m, 2H), 4.19-4.02 (m, 3H), 3.67-3.60 (m, 1H), 3.59-3.53 (m, 2H), 2.92-2.85 (m, 1H), 2.80-2.70 (m, 3H), 2.47-2.38 (m, 1H), 2.38-2.31 (m, 1H), 2.08 (t, J=7.9 Hz, 2H), 2.04-1.76 (m, 14H, AcOH), 1.74-1.41 (m, 11H), 1.41-1.14 (m, 2H), 0.91-0.74 (m, 18H).

SEQ ID NO: 30: Ala-Glu-Pro-Val-Pro-Leu acetate $^1$H NMR (600 MHZ, DMSO) δ8.29 (d, J=7.1 Hz, 1H), 7.89 (d, J=8.6 Hz, 1H), 7.79 (d, J=8.0 Hz, 1H), 4.54 (d, J=5.4 Hz, 1H), 4.42-4.38 (m, 1H), 4.37-4.28 (m, 2H), 4.09 (dd, J=14.2, 8.5 Hz, 1H), 3.66-3.46 (m, 5H), 2.28 (t, J=7.4 Hz, 2H), 2.13-1.71 (m, 16H, AcOH), 1.71-1.58 (m, 2H), 1.53-1.32 (m, 2H), 1.18 (d, J=6.9 Hz, 3H), 0.90-0.83 (m, 9H), 0.80 (d, J=6.6 Hz, 3H).

SEQ ID NO: 31: Glu-Pro-Val-Pro-Leu acetate $^1$H NMR (600 MHZ, DMSO) δ7.94-7.86 (m, 2H), 4.44 (dd, J=8.3, 4.5

Hz, 1H), 4.37-4.27 (m, 2H), 4.13 (q, J=7.6 Hz, 1H), 3.74-3.69 (m, 1H), 3.66-3.42 (m, 4H), 2.40-2.25 (m, 2H), 2.06-1.58 (m, 17H, AcOH), 1.46 (t, J=7.3 Hz, 2H), 0.89-0.84 (m, 9H), 0.81 (d, J=6.5 Hz, 3H).

SEQ ID NO: 32: Pro-Val-Pro-Leu acetate $^1$H NMR (600 MHZ, DMSO) δ8.15 (d, J=9.0 Hz, 1H), 7.91 (d, J=8.0 Hz, 1H), 4.35 (dt, J=10.1, 5.2 Hz, 2H), 4.22-4.02 (m, 1H), 3.67-3.59 (m, 2H), 3.56 (q, J=13.2, 9.3 Hz, 1H), 2.96-2.88 (m, 1H), 2.86-2.76 (m, 1H), 2.05-1.59 (m, 11H, AcOH), 1.59-1.42 (m, 2H), 0.91-0.72 (m, 12H).

SEQ ID NO: 34: Pro-Ala-Ala-Glu-Pro-Val acetate $^1$H NMR (600 MHZ, DMSO) δ 8.01 (d, J=7.3 Hz, 1H), 7.14 (d, J=7.8 Hz, 1H), 4.49 (q, J=6.8 Hz, 1H), 4.31-4.22 (m, 3H), 3.75 (dd, J=7.8, 4.7 Hz, 1H), 3.70-3.61 (m, 2H), 2.88-2.81 (m, 1H), 2.81-2.75 (m, 1H), 2.27-2.13 (m, 2H), 2.01-1.64 (m, 18H, AcOH), 1.58 (p, J=6.9 Hz, 2H), 1.17 (dd, J=10.2, 7.1 Hz, 6H), 0.78 (dd, J=6.9, 3.5 Hz, 6H).

SEQ ID NO: 35: Pro-Ala-Ala-Glu-Pro acetate $^1$H NMR (600 MHZ, DMSO) δ 8.28 (s, 1H), 8.12 (d, J=7.5 Hz, 1H), 7.90 (d, J=7.7 Hz, 1H), 4.49 (dd, J=13.7, 7.7 Hz, 1H), 4.35-4.13 (m, 3H), 3.76-3.50 (m, 3H), 2.97-2.79 (m, 2H), 2.33-2.18 (m, 2H), 2.16-1.77 (m, 10H, AcOH), 1.73-1.58 (m, 4H), 1.26-1.13 (m, 6H).

SEQ ID NO: 45: Ala-Glu-Pro-Val acetate $^1$H NMR (600 MHZ, DMSO) δ 8.36 (d, J=7.4 Hz, 1H), 7.46 (d, J=8.0 Hz, 1H), 4.65-4.53 (m, 1H), 4.35 (dd, J=8.6, 3.4 Hz, 1H), 3.89 (dd, J=7.9, 5.4 Hz, 1H), 3.74-3.53 (m, 3H), 2.38-2.19 (m, 2H), 2.05-1.64 (m, 10H, AcOH), 1.27-1.17 (m, 3H), 0.83 (d, J=7.1 Hz, 6H).

SEQ ID NO: 48: Pro-Ala-Gly-Glu-Pro-Val-Pro-Leu-Val-Lys-Gln-Asp acetate $^1$H NMR (600 MHZ, DMSO) δ 8.33 (d, J=7.6 Hz, 1H), 8.27 (d, 1H), 8.21 (t, J=5.8 Hz, 1H), 8.10 (d, J=7.5 Hz, 1H), 8.05-7.97 (m, 2H), 7.93 (d, J=8.5 Hz, 1H), 7.57 (d, J=6.4 Hz, 1H), 7.51 (d, J=8.8 Hz, 1H), 7.16 (s, 1H), 6.70 (s, 1H), 4.53-4.47 (m, 1H), 4.38 (dd, J=8.2, 4.2 Hz, 1H), 4.35-4.20 (m, 5H), 4.18-4.09 (m, 2H), 4.06 (s, 1H), 3.75-3.50 (m, 8H), 2.93-2.69 (m, 5H), 2.45-2.41 (m, 1H), 2.41-2.30 (m, 1H), 2.25 (t, J=7.3 Hz, 2H), 2.08 (t, J=7.9 Hz, 2H), 2.01-1.76 (m, 15H, AcOH), 1.74-1.53 (m, 8H), 1.53-1.40 (m, 4H), 1.33 (d, J=7.2 Hz, 2H), 1.20 (t, J=9.0 Hz, 3H), 0.91-0.73 (m, 18H).

SEQ ID NO: 50: Pro-Ala-Ala-Glu-Pro-Val-Pro-leu-Val-Lys-Gln-Asn acetate $^1$H NMR (600 MHZ, DMSO) δ 8.49 (d, J=7.8 Hz, 1H), 8.17-8.06 (m, 2H), 8.05-7.99 (m, 2H), 7.97 (d, J=7.7 Hz, 1H), 7.92 (d, J=8.7 Hz, 1H), 7.59 (s, 1H), 7.54 (d, J=8.8 Hz, 1H), 7.37 (d, J=6.9 Hz, 1H), 7.10 (s, 1H), 6.68 (d, J=15.7 Hz, 2H), 4.48 (d, J=5.1 Hz, 1H), 4.39 (dd, J=8.1, 4.3 Hz, 1H), 4.35-4.19 (m, 6H), 4.17-4.10 (m, 1H), 4.05-3.97 (m, 2H), 3.67-3.48 (m, 6H), 2.92-2.78 (m, 2H), 2.78-2.66 (m, 3H), 2.44-2.34 (m, 1H), 2.33-2.20 (m, 3H), 2.07 (t, J=7.8 Hz, 2H), 2.01-1.76 (m, 15H, AcOH), 1.75-1.62 (m, 6H), 1.62-1.53 (m, 3H), 1.49-1.29 (m, 6H), 1.19-1.12 (m, 6H), 0.91-0.73 (m, 18H).

SEQ ID NO: 51: Pro-Ala-Ala-Glu-Pro-Val-Pro-leu-Val-Val-Gln-Asp acetate $^1$H NMR (600 MHZ, DMSO) δ 8.51 (d, J=7.6 Hz, 1H), 8.08 (d, J=7.3 Hz, 1H), 8.03-7.96 (m, 2H), 7.95-7.89 (m, 2H), 7.78 (d, J=8.9 Hz, 1H), 7.75-7.69 (m, 1H), 7.61 (d, J=8.8 Hz, 1H), 7.18 (s, 1H), 6.68 (s, 1H), 4.51 (d, J=5.4 Hz, 1H), 4.40 (dd, J=8.2, 4.2 Hz, 1H), 4.35-4.12 (m, 10H), 4.01-3.95 (m, 1H), 3.69-3.51 (m, 4H), 3.09 (d, J=6.4 Hz, 2H), 2.45-2.40 (m, 1H), 2.39-2.34 (m, 1H), 2.27 (dd, J=13.4, 6.7 Hz, 2H), 2.21-2.13 (m, 1H), 2.06 (t, J=8.0 Hz, 2H), 2.02-1.75 (m, 18H, AcOH), 1.75-1.58 (m, 5H), 1.44 (t, J=7.3 Hz, 2H), 1.22 (t, J=7.1 Hz, 3H), 1.16 (d, J=7.0 Hz, 3H), 0.88 (d, J=6.7 Hz, 3H), 0.85 (dd, J=6.5, 2.7 Hz, 6H), 0.83-0.77 (m, 15H).

SEQ ID NO: 52: Pro-Ala-Ala-Glu-Pro-Val-Pro-Val-Val-Lys-Gln-Asp acetate $^1$H NMR (600 MHZ, DMSO) δ 8.28 (s, 1H), 8.17 (d, J=8.0 Hz, 1H), 8.09 (d, J=7.5 Hz, 1H), 7.99-7.92 (m, 2H), 7.87 (dd, J=16.4, 8.8 Hz, 2H), 7.68 (d, J=8.5 Hz, 1H), 7.57 (d, J=6.1 Hz, 1H), 7.17 (s, 1H), 6.70 (s, 1H), 4.50-4.45 (m, 1H), 4.44-4.35 (m, 2H), 4.32-4.21 (m, 4H), 4.18-4.10 (m, 3H), 4.08-3.99 (m, 1H), 3.66-3.49 (m, 6H), 2.90-2.82 (m, 1H), 2.82-2.72 (m, 3H), 2.46-2.30 (m, 2H), 2.27-2.23 (m, 1H), 2.07 (t, J=7.9 Hz, 2H), 2.01-1.76 (m, 19H, AcOH), 1.75-1.60 (m, 5H), 1.60-1.45 (m, 5H), 1.39-1.25 (m, 2H), 1.20-1.10 (m, 6H), 0.88 (d, J=6.6 Hz, 3H), 0.86-0.76 (m, 15H).

SEQ ID NO: 56: Pro-Ile-Ala-Glu-Pro-Val-Pro-Leu-Val-Lys-Gln-Asp acetate $^1$H NMR (600 MHZ, DMSO) δ 8.27 (d, J=7.8 Hz, 1H), 8.17 (d, J=7.3 Hz, 1H), 8.10 (d, J=9.4 Hz, 1H), 8.05-7.97 (m, 2H), 7.92 (q, J=13.5, 8.1 Hz, 2H), 7.57 (d, J=6.3 Hz, 1H), 7.51 (d, J=8.8 Hz, 1H), 7.16 (s, 1H), 6.70 (s, 1H), 4.54-4.45 (m, 1H), 4.39 (dd, J=8.3, 4.2 Hz, 1H), 4.35-4.22 (m, 5H), 4.21-4.09 (m, 3H), 4.10-4.00 (m, 1H), 3.67-3.48 (m, 6H), 3.41-3.16 (m, 4H), 2.95-2.86 (m, 1H), 2.81-2.68 (m, 3H), 2.47-2.41 (m, 1H), 2.41-2.32 (m, 1H), 2.25 (t, J=7.6 Hz, 2H), 2.08 (t, J=7.9 Hz, 2H), 2.02-1.75 (m, 19H, AcOH), 1.75-1.55 (m, 9H), 1.54-1.36 (m, 5H), 1.33 (d, J=7.0 Hz, 2H), 1.15 (d, J=7.1 Hz, 3H), 0.89-0.784 (m, 8H), 0.82-0.76 (m, 14H).

SEQ ID NO: 57: Pro-Ala-Ala-Glu-Pro-Val-Pro-Leu-Val-Lys-Glu-Asp acetate $^1$H NMR (600 MHZ, DMSO) δ 8.31 (d, J=7.8 Hz, 1H), 8.20 (d, J=7.8 Hz, 1H), 8.09 (d, J=7.5 Hz, 1H), 8.03 (t, J=7.7 Hz, 2H), 7.96-7.87 (m, 2H), 7.58 (d, J=6.3 Hz, 1H), 7.49 (d, J=8.8 Hz, 1H), 4.49 (q, J=5.3 Hz, 1H), 4.39 (dd, J=8.2, 4.4 Hz, 1H), 4.35-4.20 (m, 7H), 4.19-4.12 (m, 2H), 4.10-4.00 (m, 1H), 3.67-3.49 (m, 7H), 2.91-2.84 (m, 2H), 2.84-2.70 (m, 4H), 2.46-2.38 (m, 1H), 2.38-2.33 (m, 1H), 2.29-2.18 (m, 4H), 2.04-1.76 (m, 19H, AcOH), 1.76-1.55 (m, 8H), 1.55-1.41 (m, 5H), 1.32 (s, 2H), 1.21-1.11 (m, 6H), 0.94-0.73 (m, 18H).

SEQ ID NO: 58: Pro-Ala-Ala-Glu-Pro-Val-Pro-Leu-Val-Lys-Asn-Asp acetate $^1$H NMR (600 MHz, DMSO) δ 8.28 (d, J=7.1 Hz, 1H), 8.19 (d, J=7.7 Hz, 1H), 8.09 (d, J=7.5 Hz, 1H), 8.04 (d, J=7.7 Hz, 1H), 8.00-7.89 (m, 3H), 7.50 (d, J=8.6 Hz, 1H), 7.44 (d, J=6.0 Hz, 1H), 7.30 (s, 1H), 6.80 (s, 1H), 4.56-4.46 (m, 2H), 4.38 (dd, J=8.1, 4.3 Hz, 1H), 4.35-4.20 (m, 6H), 4.18-4.12 (m, 1H), 4.04-4.00 (m, 1H), 3.66-3.49 (m, 6H), 2.93-2.84 (m, 1H), 2.83-2.71 (m, 3H), 2.43-2.31 (m, 3H), 2.25 (t, J=8.0 Hz, 2H), 2.04-1.57 (m, 26H, AcOH), 1.56-1.46 (m, 3H), 1.46-1.43 (m, 2H), 1.35-1.27 (m, 2H), 1.20-1.10 (m, 6H), 0.86 (dd, J=14.8, 7.9 Hz, 9H), 0.81-0.76 (m, 9H).

SEQ ID NO: 60: Pro-Ala-Ala-Glu-Pro-Val-Pro-Leu-Val-Lys-Gln-Glu acetate $^1$H NMR (600 MHz, DMSO) δ 8.51 (d, J=8.0 Hz, 1H), 8.17 (d, J=7.8 Hz, 1H), 8.10 (d, J=7.4 Hz, 1H), 8.04 (d, J=6.2 Hz, 2H), 7.96 (d, J=7.7 Hz, 1H), 7.93 (d, J=8.5 Hz, 1H), 7.52 (d, J=8.8 Hz, 1H), 7.34 (d, J=6.6 Hz, 1H), 7.11 (s, 1H), 6.71 (s, 1H), 4.48 (d, J=5.4 Hz, 1H), 4.39 (dd, J=8.1, 4.3 Hz, 1H), 4.34-4.18 (m, 7H), 4.18-4.10 (m, 1H), 4.07-3.99 (m, 1H), 3.83 (q, J=12.8, 6.5 Hz, 2H), 3.69-3.48 (m, 7H), 2.92-2.83 (m, 1H), 2.81-2.62 (m, 4H), 2.31-2.02 (m, 7H), 2.01-1.75 (m, 22H, AcOH), 1.74-1.25 (m, 16H), 1.20-1.11 (m, 6H), 0.91-0.83 (m, 9H), 0.81-0.76 (m, 9H).

SEQ ID NO: 62: Pro-Ala-Ile-Glu-Pro-Val-Pro-Leu-Val-Lys-Gln-Asp acetate $^1$H NMR (600 MHZ, DMSO) δ 8.31-8.23 (m, 1H), 8.20 (d, J=7.5 Hz, 1H), 8.03 (d, J=7.7 Hz, 2H), 7.99 (d, J=7.6 Hz, 1H), 7.93-7.85 (m, 2H), 7.57 (d, J=6.6 Hz, 1H), 7.51 (d, J=8.1 Hz, 1H), 7.16 (s, 1H), 6.70 (s, 1H), 4.49 (d, J=5.5 Hz, 1H), 4.41-4.20 (m, 6H), 4.19-4.00 (m, 5H), 3.71-3.61 (m, 2H), 3.61-3.47 (m, 4H), 2.91-2.73 (m, 4H), 2.45-2.39 (m, 1H), 2.39-2.29 (m, 1H), 2.24 (t, J=7.1 Hz, 2H), 2.07 (t, J=7.9 Hz, 2H), 2.02-1.76 (m, 20H, AcOH), 1.74-1.47 (m, 12H), 1.47-1.29 (m, 5H), 1.16 (d, J=6.9 Hz, 3H), 1.04 (d, J=8.4 Hz, 1H), 0.89-0.84 (m, 8H), 0.83-0.72 (m, 16H).

SEQ ID NO: 66: Pro-Ala-Ala-Glu-Pro-Val-Pro-Leu-Val-Arg-Gln-Asp acetate $^1$H NMR (600 MHz, DMSO) δ 9.30 (s, 1H), 8.39 (d, J=8.7 Hz, 1H), 8.19 (d, J=7.9 Hz, 1H), 8.09 (d, J=7.4 Hz, 1H), 8.03 (d, J=8.1 Hz, 1H), 7.98 (d, J=7.0 Hz, 1H), 7.96-7.89 (m, 3H), 7.52 (d, J=8.9 Hz, 1H), 7.11 (s, 1H), 6.69 (s, 1H), 4.49 (d, J=5.3 Hz, 1H), 4.39 (dd, J=8.2, 4.3 Hz, 1H), 4.34 (d, J=4.3 Hz, 1H), 4.31-4.21 (m, 5H), 4.20-4.10 (m, 3H), 3.68-3.49 (m, 6H), 3.13 (d, J=6.1 Hz, 1H), 3.00-2.93 (m, 1H), 2.92-2.85 (m, 1H), 2.83-2.76 (m, 1H), 2.41-2.32 (m, 1H), 2.25 (t, J=8.2 Hz, 2H), 2.09-2.03 (m, 2H), 2.02-1.76 (m, 20H, AcOH), 1.74-1.70 (m, 1H), 1.69-1.56 (m, 7H), 1.55-1.39 (m, 4H), 1.22-1.11 (m, 6H), 0.93-0.83 (m, 9H), 0.83-0.77 (m, 9H).

SEQ ID NO: 73: Val-Pro-Leu-Val acetate $^1$H NMR (600 MHZ, MeOD) δ 4.54-4.49 (m, 1H), 4.40 (dd, J=9.2, 6.0 Hz, 1H), 4.18 (d, J=5.0 Hz, 1H), 3.99 (d, J=5.3 Hz, 1H), 3.69 (dd, J=10.7, 5.0 Hz, 1H), 3.65-3.58 (m, 1H), 2.32-2.20 (m, 2H), 2.19-2.01 (m, 3H), 2.00-1.86 (m, 4H, AcOH), 1.85-1.75 (m, 1H), 1.69-1.54 (m, 2H), 1.12 (d, J=7.0 Hz, 3H), 1.03-1.01 (m, 3H), 0.95 (d, J=6.6 Hz, 3H), 0.93-0.89 (m, 9H).

Example 2: Anti-Ulcer Effect of Polypeptide (SEQ ID NO: 1) on Ethanol-Induced Gastric Ulcer in Mice 1. Experimental animal: SPF grade C57BL/6 mice, from Chengdu Yaokang Biotechnology Ltd, animal license number: SCXK (Chuan) 2020-034.

2. Method: After adaptive feeding, the mice were randomly divided into four groups with 10 mice in each group, namely, control group (normal group), model group (modeling with absolute ethanol), positive drug group (teprenone 160 mg/kg) and SEQ ID NO: 1 group (1 mg/kg). After the animals were grouped, the control group and model group were treated with pure water, and the other dosed groups were treated with the corresponding drugs once a day for 8 consecutive days. On the 7th day, after treatment, all the animals were fasted for 24 h with free access to water. On the 8th day, 30 min after administration, the mice in each group (except the control group) were given 0.15 mL of absolute ethanol by oral gavage; and after 1 h, the animals were sacrificed by excessive $CO_2$ inhalation, the gastric cardia was ligated, the pylorus was occluded, and the whole stomach was removed. 1 mL of 1% formaldehyde solution was injected into the gastric lumen, the cardia was ligated, and the stomach was taken out and immediately immersedd in 1% formaldehyde solution for fixation of 25 min. The stomach was cut open along the greater curvature, the content of the stomach was cleaned off with normal saline, and the ulcer index was calculated after being laid flat. Calculation method for ulcer index: If the length of cord-like injury was greater than 1 mm, the length thereof was measured, with 1 point per millimeter; if the width thereof was greater than 1 mm, the score thereof was doubled according to the number of millimeters of the width; and if the length was less than 1 mm, a score of 0.5 was given, and the scores were added up to obtain the ulcer index of the animal.

Figure 2:
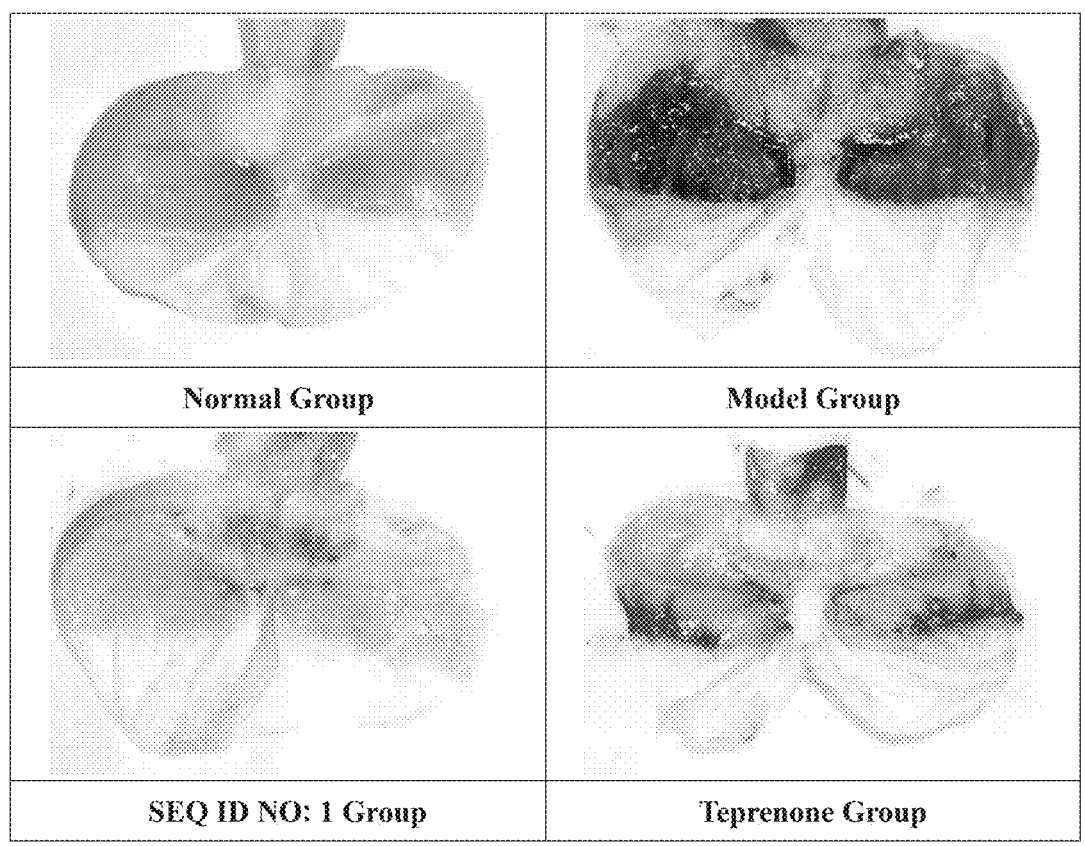
FIG. 2 shows the anti-ulcer effect of the compound of SEQ ID NO: 1 on ethanol-induced gastric ulcer in mice.

3. Results:
In the mouse ethanol-induced gastric ulcer model, oral gavage of the compound of SEQ ID NO: 1 once a day for 8 consecutive days could significantly reduce the gastric ulcer index of mice, and the effect was greater than that of the positive drug group (Table 6). The results showed that the compound of SEQ ID NO: 1 had a significant effect on treating gastric ulcer. The experimental results were shown in FIG. 2.

TABLE 6

Effects of test drugs on the ulcer index of mice with ethanol-induced gastric ulcer (n = 10, $\bar{x} \pm s$)

| Group | Ulcer index |
| --- | --- |
| Control group | 1.84 ± 1.62 |
| Model group | 35.32 ± 23.30## |
| Teprenone group: | 13.42 ± 7.61* |
| SEQ ID No: 1 group | 8.13 ± 4.17** |

Note:,
$P < 0.01$, compared with the control group; and
*$P < 0.05$,
**$P < 0.01$, compared with the model group.

Example 3: Anti-Ulcer Effect of Some Polypeptide Samples Obtained from Example 1 on Ethanol-Induced Gastric Ulcer Model in Mice 1. Experimental animal: SPF grade C57BL/6 mice, from Chengdu Yaokang Shengwu Keji Youxian Gongsi, animal license number: SCXK (Chuan) 2020-034.

2. Method:
After adaptive feeding, all the animals were fasted for 24 h with free access to water after administration one day before the experiment. Before modeling, the experimental mice were randomly divided into groups: blank group (5 mice), model group (10 mice), and treatment groups (10 mice per group). Except for the blank group and the model group, which were given sterile water by gavage, the treatment groups were administered with different test compounds by gavage at a dose of 0.2 mg/kg, respectively. One hour after administration, the mice received 0.9 ml/kg absolute ethanol by oral gavage for modeling. After 1 h, the animals were sacrificed by cervical dislocation, the gastric cardia was ligated, the pylorus was occluded, and the whole stomach was removed. 1 mL of 1% formaldehyde solution was injected into the gastric lumen, the cardia was ligated, and the stomach was taken out and immediately immersed in 1% formaldehyde solution. After 30 min, the stomach tissue was taken out and cut open along the greater curvature. The content of the stomach was rinsed off with normal saline, the injury of gastric mucosa in mice were observed and measured after being laid flat, and the ulcer index and ulcer inhibition rate were calculated.

Calculation method for ulcer index: If the length of cord-like injury was greater than 1 mm, the length thereof was measured, with 1 point per millimeter; if the width thereof was greater than 1 mm, the score thereof was doubled according to the number of millimeters of the width; and if the length was less than 1 mm, a score of 0.5 was given, and the scores were added to obtain the ulcer index of the animal.

Ulcer inhibition rate=(ulcer index of model group-ulcer index of treatment group)/ulcer index of model group*100%; and Relative ulcer inhibition rate=(ulcer inhibition rate of test compound)/(ulcer inhibition rate of Compound 1).

3. Results: Table 7 showed the relative ulcer inhibition rates of the compounds of the present invention

TABLE 7

Anti-ulcer activity of single administration in ethanol-induced model in mice

| SEQ ID NO: | Anti-ulcer activity * |
|---|---|
| 1 | +++ |
| 2 | ND |
| 3 | +++ |
| 4 | ND |
| 5 | ND |
| 6 | ND |
| 7 | ND |
| 8 | + |
| 9 | ND |
| 10 | ++++ |
| 11 | ++ |
| 12 | / |
| 13 | ND |
| 14 | ND |
| 15 | ND |
| 16 | ND |
| 17 | ND |
| 18 | ND |
| 19 | ND |
| 20 | ND |
| 21 | ND |
| 22 | ND |
| 23 | ND |
| 24 | ND |
| 25 | ND |
| 26 | +++ |
| 27 | +++ |
| 28 | +++ |
| 29 | ND |
| 30 | +++ |
| 31 | +++ |
| 32 | +++ |
| 33 | ND |
| 34 | / |
| 35 | + |
| 36 | ND |
| 37 | ND |
| 38 | +++ |
| 39 | ND |
| 40 | ND |
| 41 | ND |
| 42 | ND |
| 43 | ND |
| 44 | + |
| 45 | – |
| 46 | ND |
| 47 | ND |
| 48 | ++ |
| 49 | ND |
| 50 | / |
| 51 | ND |
| 52 | ND |
| 53 | ND |
| 54 | ND |
| 55 | ND |
| 56 | – |
| 57 | ++ |
| 58 | / |
| 59 | ND |
| 60 | ND |
| 61 | ND |
| 62 | ND |
| 63 | ND |
| 64 | + |
| 65 | ND |
| 60 | + |
| 67 | + |
| 68 | ND |
| 69 | ND |
| 70 | ND |
| 71 | ND |
| 72 | ND |
| 73 | ++ |

* Note:
The anti-ulcer effect of each compound was completed by several cohorts of experiments. For easy comparison, the anti-ulcer activity was expressed as the mean value of the relative ulcer inhibition rate (the compound of SEQ ID NO: 1 was used as a control group in each cohort of experiments).
Relative ulcer inhibition rate = (ulcer inhibition rate of test compound)/(ulcer inhibition rate of compound of SEQ ID NO: 1)
Relative ulcer inhibition rate >1.20, denoted as "++++";
relative ulcer inhibition rate 0.9-1.20, denoted as "+++";
relative ulcer inhibition rate 0.6-0.9, denoted as "++";
relative ulcer inhibition rate 0.3-0.6, denoted as "+";
0< relative ulcer inhibition rate <0.3, denoted as "/" (very low activity);
relative ulcer inhibition rate <0, denoted as "–"; and
ND represented no comparison with compound of SEQ ID NO: 1.

Example 4: Effect of the Compound of SEQ ID NO: 1 on Mouse Gastric Organoid

Method: The gastric antrum epithelium of healthy wild-type mice was used for organoid culture. The epithelial layer of the gastric antrum of the mice was separated from the muscle layer under stereoscope, cut into small pieces about 0.5 mm in size, and digested with 2.5 mM EDTA/DPBS at 4° C. for about 1 h. The digested gastric glandular epithelial cells were filtered and centrifuged, and the supernatant was discarded. The obtained cell pellet was resuspended in matrix gel and seeded in a culture dish followed by addition of organoid medium containing growth factors. In the control group, no test drug was added except growth factors. In the experimental group, the compound of SEQ ID NO: 1 was added under the same culture conditions as in the control group. The ball formation and organoid growth were observed and photographed at Day 1, Day 3, Day 5 and Day 7 with an inverted microscope, and the effect of the compound of SEQ ID NO: 1 on organoid growth was assessed.

Figure 3:
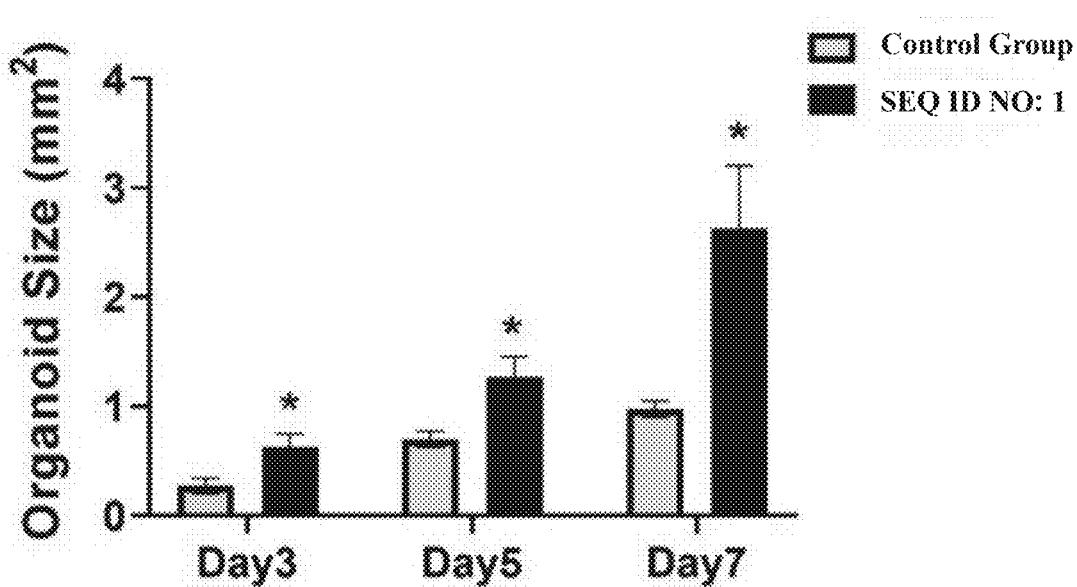
FIG. 3 shows the results of the compound of SEQ ID NO: 1 on promoting the proliferation and differentiation of gastric organoids.
Figure 4:
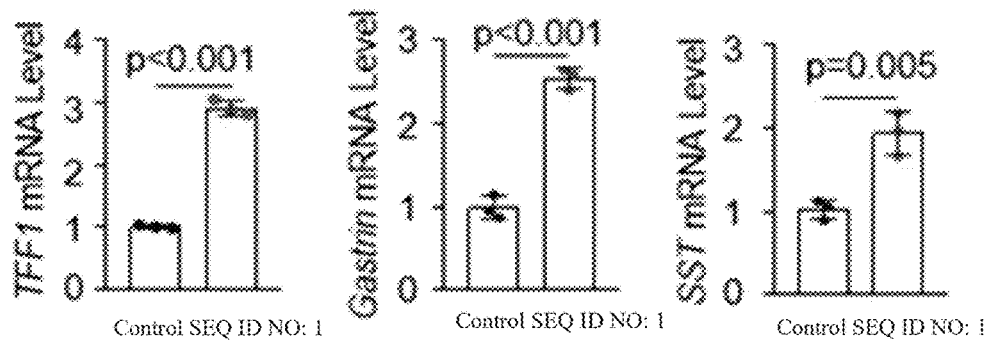
FIG. 4 shows the results of the compound of SEQ ID NO: 1 promoting the differentiation of gastric organoids.

Results: Compared with the control group, the growth rate of the organoids in the culture medium containing the compound of SEQ ID NO: 1 was obviously accelerated over time. Through the quantitative analysis of the diameter of each organoids, the results showed that the volume of the organoids treated with the compound of SEQ ID NO: 1 was significantly larger than that of the control group (see FIG. 3, *$p<0.05$, compared with the control group), and the proliferation of the organoids could be significantly promoted (all the statistical data also showed significant difference). RNA was extracted from the organoids, and the transcription level of target genes was detected by real-time fluorescence quantitative PCR. It was discovered that the mRNA levels of the endocrine cell markers SST and Gastrin and the neck mucus cell marker TFF2 increased significantly (see FIG. 4). These results indicated that the polypeptide the compound of SEQ ID NO: 1 could promote the proliferation and differentiation of gastric organoid, indicating that the compound of SEQ ID NO: 1 participated in and regulated the proliferation and differentiation of gastric epithelial stem cells.

Example 5: Therapeutic Effect of the Compound of SEQ ID NO: 1 on Chronic Atrophic Gastritis Model in Mice Method: Chronic atrophic gastritis (Lgr5-GFP-CreERT mice) was induced by MNNG (N-methyl-N-nitro-N-nitrosoguanidine) combined with ranitidine. The mice were free to access to an aqueous solution containing MNNG (100 mg/ml), and at the same time, the mice were given ranitidine (8 mg/ml) aqueous solution at a dose of 150 mg/kg by gavage at a fixed time per day for 20 consecutive weeks. After 20 weeks of modeling, on the basis of drinking ordinary distilled water, the mice were given the compound of SEQ ID NO: 1 (5 mg/kg) daily by gavage. After 2 weeks of administration, the therapeutic effect of the compound of SEQ ID NO: 1 on chronic atrophic gastritis was observed.

Figure 5:
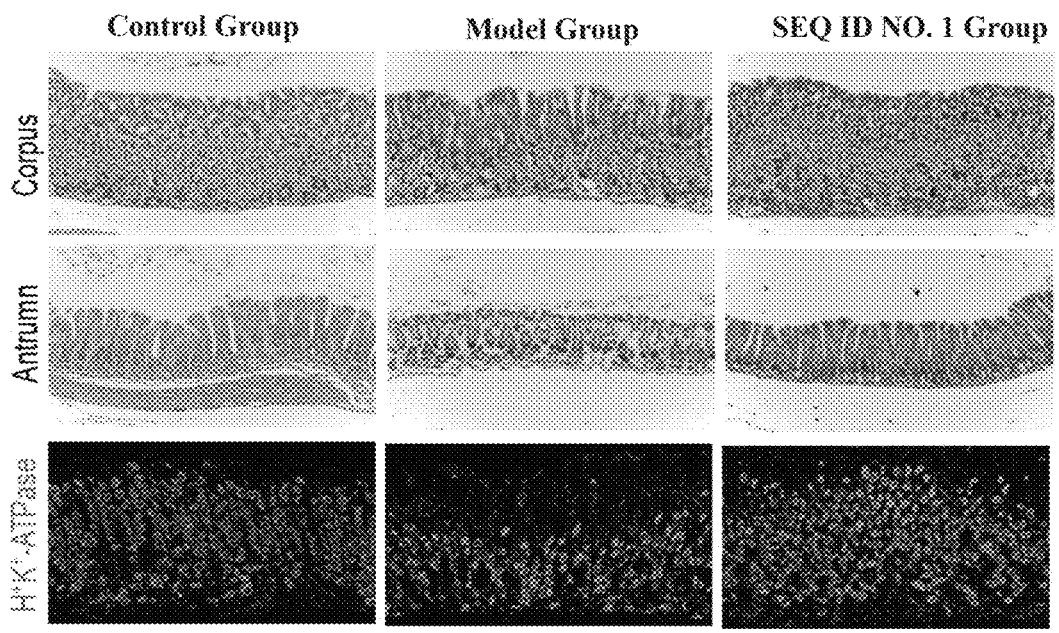
FIG. 5 shows the therapeutic effect of the compound of SEQ ID NO: 1 on mice with chronic atrophic gastritis.

Results: The results of tissue staining showed that the gland structure in the corpus and antrum of model group was disordered, accompanied by a reduced number of parietal cells ($H^+$—$K^+$-ATPase positive) and decreased height of the mucosal epithelium in the gastric antrum. After 2 weeks of treatment with the compound of SEQ ID NO: 1, compared with the model group, the structure of the gastric was recovered to normal, the number of parietal cells increased significantly, and the height of the mucosa in the gastric antrum was substantially recovered to the normal state. The results were shown in FIG. 5. These results indicated that the compound of SEQ ID NO: 1 could promote the repair of chronic atrophic gastritis in mice.

Figure 6:
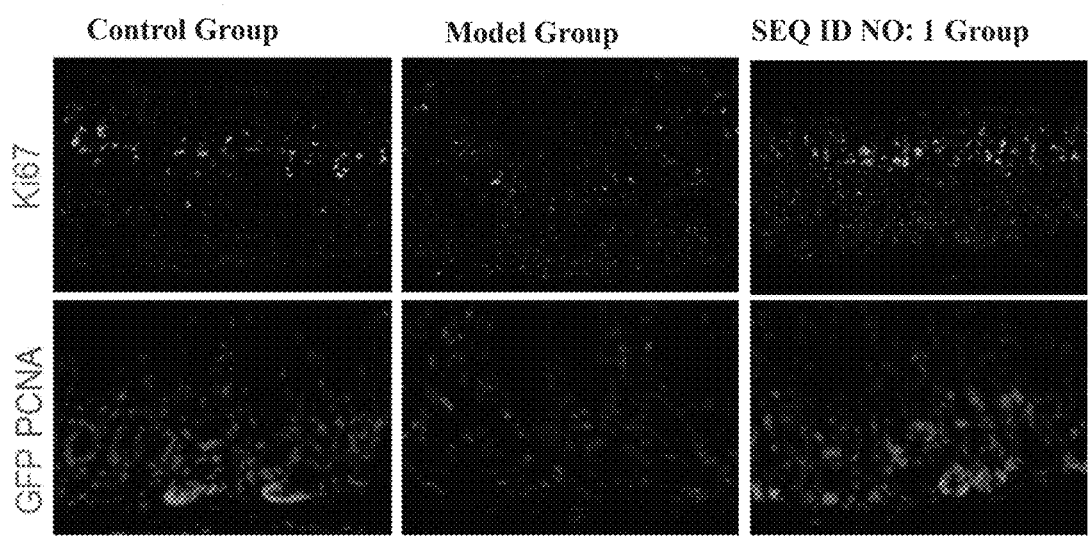
FIG. 6 shows the effect of the compound of SEQ ID NO: 1 on gastric epithelial stem cells in rats with chronic atrophic gastritis.

In chronic atrophic gastritis, the epithelial repair process entails stem cells. We detected the change in the gastric epithelial stem cells ($Lgr5^+$ and $AQP5^+$) by immunofluorescence staining. The experimental results showed that compared with the control group, the number of stem cells in the model group decreased significantly; and compared with the model group, the number of proliferatively active stem cells (PCNA-positive $Lgr5^+$ cells and Ki67-positive $AQP5^+$ cells) in the the compound of SEQ ID NO: 1 treatment group also increased significantly, and all the statistical results had significant difference. The results were shown in FIG. 6.

Example 6: Therapeutic Effect of the Compound of SEQ ID NO: 1 on Rats with Chronic Atrophic Gastritis 1. Experimental Animals 85 SPF grade SD rats, half male and half female, weighing 160-280 g, were provided by SPF (Beijing) Biotechnology Co., Ltd. with the license number: SCXK (Jing) 2016-0002.

2. Experimental Method

85 SD rats were fed adaptively for one week and then randomly divided into a blank control group (10 rats) and a chronic atrophic gastritis model group (abbreviated as CAG group) (75 rats). The blank control group was given 5 ml/kg deionized water daily by gavage, with normal diet and free access to water. The CAG group was given 120 μg/mL MNNG (N-methyl-N-nitro-N-nitrosoguanidine) aqueous solution daily by gavage, at 5 ml/kg, with free access to 0.03% ranitidine feed, 2% sodium salicylate and water. After fasting for 18 hours every week from the 15th week, a hot starch paste (5 ml/kg, 60-70° C.), instead of MNNG, was given by gavage. The rest treatment was the same as hereinbefore. From the 18th week, two male and two female rats in the model group were randomly selected every two weeks, the gastric mucosa was taken for pathological evaluation until the model was successful (reduction of intrinsic glands+intestinal metaplasia), and 19 rats died during the modeling process. At the 25th week of modeling, the CAG rats were randomly divided into three groups: a model group, a the compound of SEQ ID NO: 1 high-dose group (3 mg/kg) and a low-dose SEQ ID NO: 1 group (1 mg/kg). The normal control and model groups were given the same volume of normal saline by gavage daily, and each of the other groups was given the corresponding drug by gavage for 8 weeks.

During the experiment, the weight changes of the rats were recorded, the food intake and water consumption were measured every week, the activity status of the rats was observed, etc., at regular intervals every week. After 8 weeks of administration, the rats were fasted for 24 hours with free access to water and were anesthetized by intraperitoneal injection of 10% chloral hydrate at 3.5 ml/kg. The whole stomach was removed, then quickly cut open along the greater curvature, and rinsed with normal saline, and gastric mucosa tissues were taken from the whole lesser curvature and the near greater curvature up from the esophagus end down to the duodenum end, fixed in 10% neutral formalin solution, conventionally embedded with paraffin, sectioned and conventionally stained with HE, and the pathological results were analyzed.

All data were processed by SPSS23 software. The measurement data was subjected to normality test by Shapiro-Wilk test. If it conformed to normal distribution, it was expressed by the mean±standard deviation ($\bar{X}±S$). The mean values were compared between multiple groups by One-way ANOVA. Those with equal variances were compared between groups by LSD method, while those without equal variances were compared between groups by Dunnett's T3 method. $P<0.05$ indicated that the difference was statistically significant. If it did not conform to normal distribution, rank sum test was performed, Kruskal-Wallis test was used for comparison between multiple groups, and Mann-Whitney test was used for pairwise comparison between groups. The grade data was the same as in the test method of non-normal distribution. $P<0.05$ indicated that the difference was statistically significant.

3. Results 3.1 General Condition of Rats

The rats in the normal group had smooth and dense body hair and white and shiny hair color. The degree of activity was relatively high, and the responsiveness to activities such as rearing cage movement and feeding with food and water, and sounds was high. The mental state was good, and the mood was stable during gavage, weighing and other operations. The body hair of the rats in the model group was withered, sparse and easy to fall off and had a dull and beige color. The rats had low mobility, liked to curl up and had low responsiveness to activities such as rearing cage movement and feeding with food and water, and the mental state thereof was sluggish. The rats were prone to mood swings and the behavior of biting and scratching the experiment operators during gavage, weighing and other operations. The low- and high-dose SEQ ID NO: 1 groups both improved the whole condition of the rats, e.g., in terms of mobility and responsiveness, to various extents.

3.2 Weight of Rats

After 8 weeks of administration, there was no significant difference in the weights of the female rats in each group. Compared with the normal group, the weights of the male rats in the model group significantly decreased ($P<0.05$); compared with the model group, the weights of the male rats in the low- and high-dose SEQ ID NO: 1 groups significantly increased (P<0.05), and in each of the other groups, the difference in weight was not statistically significant, as shown in Table 8.

TABLE 8

Weight (g) in each group after 8 weeks of administration

| Group | Number of animals | Weight of female rat (mean) | Weight of male rat (mean) |
|---|---|---|---|
| Blank control group | 10 | 364 | 602 |
| Model group | 12 | 369 | 446# |
| SEQ ID NO: 1, high | 14 | 396 | 637* |
| SEQ ID NO: 1, low | 14 | 374 | 532* |

Note:
$P < 0.05$, compared with the normal group; and
*$P < 0.05$, compared with the model group.

3.3 Pathological Results

Figure 7:
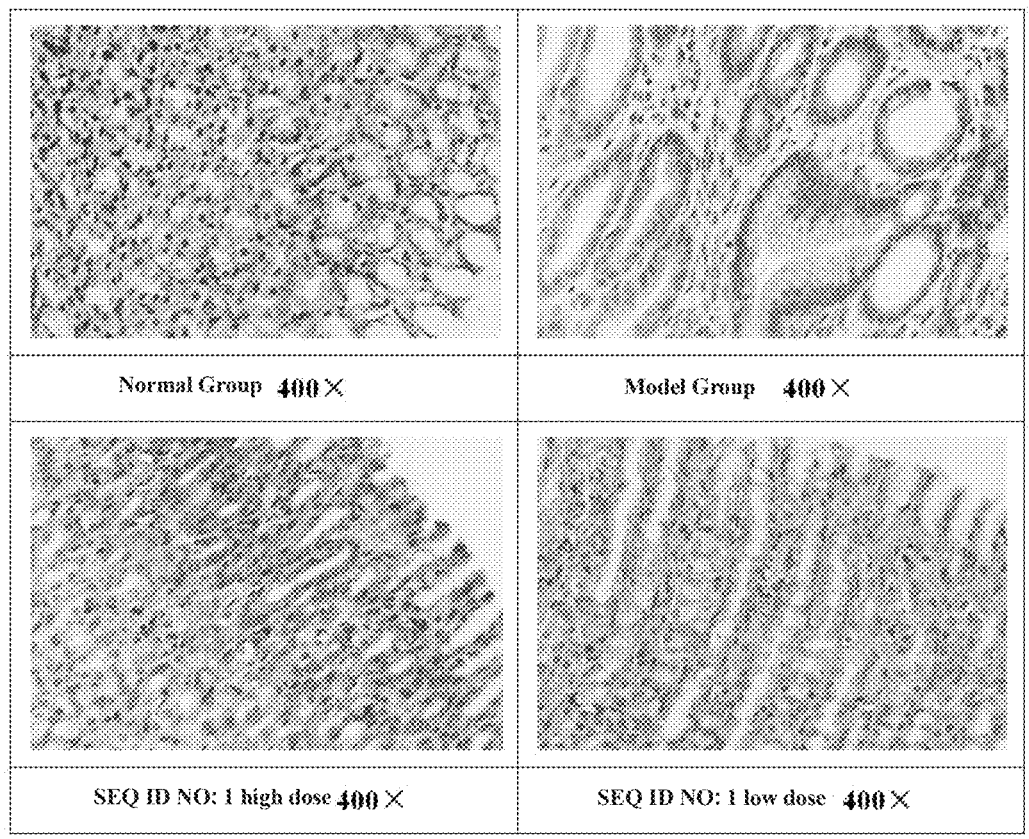
FIG. 7 shows the therapeutic effect of the compound of SEQ ID NO: 1 on rats with chronic atrophic gastritis.

Microscopic observation of pathological sections of gastric mucosa in rats: The rats in the normal group had a clear structure of each layer in the mucosa, compact and orderly arrangement of glands, and no chronic inflammation in the mucosal layer; and the rats in the model group had inflammatory cell infiltration in gastric mucosa, mucosal muscle hyperplasia, various degrees of reduction of glands in lamina propria, sparse and irregular arrangement, dilation of some glands, no intestinal metaplasia, and dysplasia in few cases. The scores of inflammation and atrophy in the model group were significantly increased (P<0.05); and compared with the model group, the low- and high-dose SEQ ID NO: 1 groups could significantly improve the degree of inflammation and atrophy of gastric mucosa in rats (P<0.05). The results were shown in FIG. 7.

Example 7: Effect of the Compound of SEQ ID NO: 1 on the Proliferation of HaCAT Cells Method: HaCAT cells were adjusted to a concentration of $1.0*10^5$ to $5.0*10^5$/mL for passaging and cultured at 37° C. and 5% $CO_2$ for 24-36 hours for biological activity detection. The cells were digested by trypsin, collected, prepared into a concentration of $2.5*10^4$/mL with a serum-free medium, seeded in a 96-well cell culture plate with 100 μL per well, i.e., 2500 cells/well, and cultured overnight at 37° C. and 5% $CO_2$. 50 μL of a compound solution formulated with the serum-free medium was further added to make the final concentration of the compound of SEQ ID NO: 1 0.4 ug/mL. An EGF control group was performed in parallel by adding 50 μL of a recombinant human epidermal growth factor (EGF) with a final concentration at 100 ng/mL. In the model control group, an equal volume of serum-free medium was added. After culturing at 37° C. and 5% $CO_2$ for 72 hours, the proliferation of the HaCAT cell line was detected by the CellTiter-Glo® kit.

Figure 8:
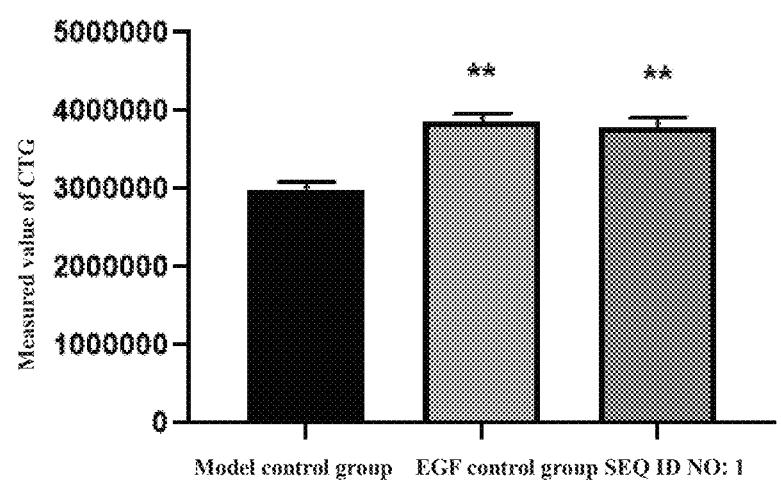
FIG. 8 shows the proliferation-promoting effect of the compound of SEQ ID NO: 1 on HaCAT cells.

Results: As shown in FIG. 8, 0.4 μg/mL the compound of SEQ ID NO: 1 had a significant proliferation-promoting effect on HaCAT cells, indicating that the compound of SEQ ID NO: 1 had a good effect on epidermal growth and skin injury repair. In FIG. 8, compared with the model control group, * represented p<0.05, and ** represented p<0.01.

Example 8: Repair Effect of Compounds 1 and 26 on Vascular Injury in Zebrafish

Figure 9:
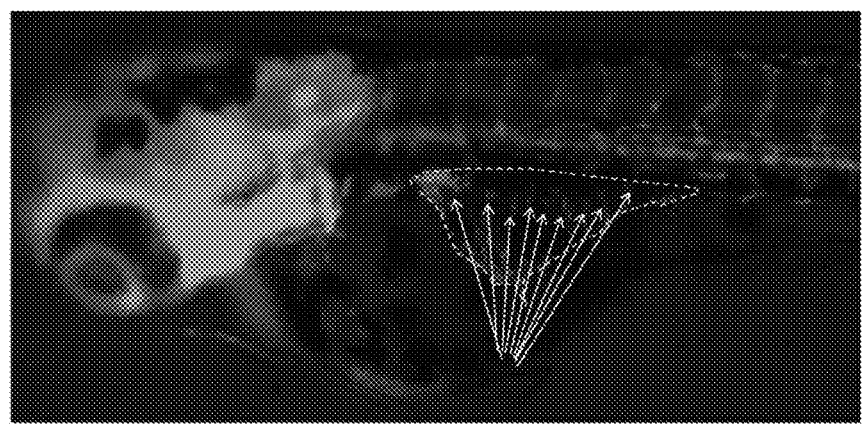
FIG. 9 shows a schematic diagram of the analysis site of the subintestinal vascular area of zebrafish.

Method: The blood vessels of transgenic vascular green fluorescent zebrafish (Fli-1) were labeled by green fluorescent protein, which was clearly visible under a fluorescence microscope (FIG. 9, the dotted frame in FIG. 9 (yellow in the original picture) was the intestinal blood vessel at the analysis site, and the arrow (white in the original picture) pointed to subintestinal vascular branches), and it became a model organism for observing vascular change. Zebrafish Fli-1 was naturally mated in pairs for breeding. Zebrafish Fli-1 was randomly selected and placed in a 6-well plate one day after fertilization, with 30 fish per well (experimental group). The zebrafish in the normal control group were treated with standard dilution water, and each of the other experimental groups was induced with aqueous simvastatin for 3 hours to establish a zebrafish microvascular loss model. After 3 hours, the aqueous solutions in all the groups were replaced with standard dilution water, and simvastatin induction was terminated. The test drug groups were respectively given the compound of SEQ ID NO: 1 (500 ng/fish) or Compound 26 (500 ng/fish) by intravenous injection and treated at 28° C. for 2 days. Ten zebrafish in each group were randomly selected and photographed under the fluorescence microscope. NIS-Elements D 3.20 advanced image processing software was used for analysis and data collection, and the number of subintestinal vascular branches was analyzed.

Figure 10:
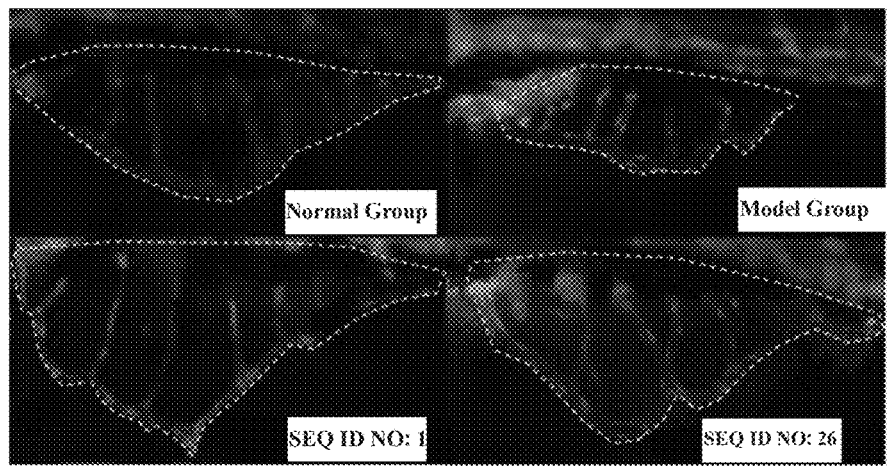
FIG. 10 shows a typical diagram of the area of the subintestinal vascular area of zebrafish treated with the compound of the present invention.
Figure 11:
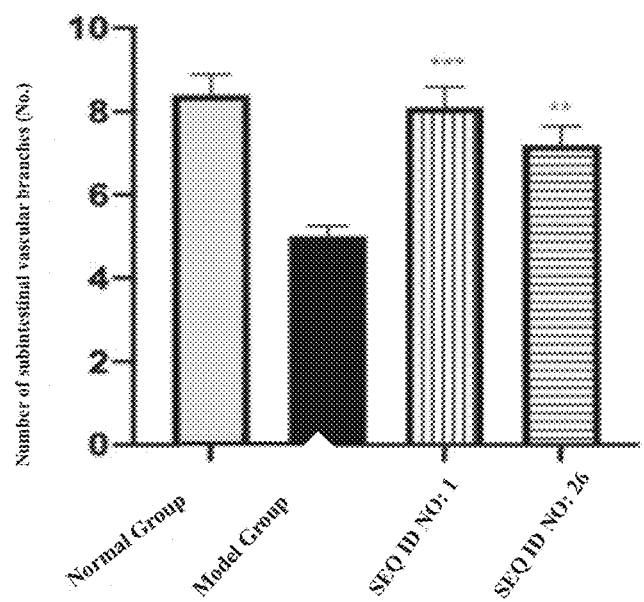
FIG. 11 shows the number of subintestinal vascular branches of zebrafish treated with the compound of the present invention.

Results: In the model group, it could be seen that the number of subintestinal vascular branches decreased. Intravenous injection of Compounds 1 and 26 could significantly reverse subintestinal microvascular loss caused by simvastatin and restore the number of subintestinal vascular branches of zebrafish. Compounds 1 and 26 were shown to promote the repair of injured blood vessels (FIGS. 10 and 11). In FIG. 11, compared with the model control group, p<0.01 and *p<0.001.

Example 9: Gastric and Intestinal Stability Test of Some Polypeptide Samples

Method: 1 mg of each of the samples to be tested (Compounds 1, 26, 27 and 28 and EGF) were taken and dissolved in 1 ml of water. 100 ul of sample solution was taken, 900 ul of water was added, and they were uniformly mixed, as a control solution. 100 ul of each sample solution was taken, and 900 ul of artificial gastric juice (W), artificial intestinal juice (X), povidone-iodine solution (I), and hydrogen peroxide solution (O) were respectively added. The solution was placed in a constant temperature water bath at 37° C. for 1 hour, and left to stand for cooling and filtering, as a test solution. The peak areas of the sample before and after treatment were respectively detected by high performance liquid chromatography, and the experimental results were compared based on the peak areas of the samples. The original solution without any treatment after being diluted with water was used as a control, and the changes in the peak areas (contents) of test solutions at corresponding positions were compared and counted.

TABLE 9

Gastric and intestinal stability test of polypeptide samples

| NO: | W Retained % | X Retained % | I Retained % | O Retained % |
|---|---|---|---|---|
| SEQ ID NO: 1 | 96 | 0 | 101 | 100 |
| SEQ ID NO: 26 | 100 | 103 | 101 | 102 |

TABLE 9-continued

Gastric and intestinal stability test of polypeptide samples

| NO: | W Retained % | X Retained % | I Retained % | O Retained % |
|---|---|---|---|---|
| SEQ ID NO: 27 | 97 | 0 | 100 | 101 |
| SEQ ID NO: 28 | 96 | 0 | 99 | 99 |
| EGF | 0 | 0 | 0 | 0 |

Note:
W represented artificial gastric juice, X represented artificial intestinal juice, I represented povidone-iodine solution, and O represented hydrogen peroxide solution.

Results: As shown in Table 9, the four test products (SEQ ID Nos: 1, 26, 27, and 28) all retained 100% in the artificial gastric juice (W), povidone-iodine solution (I) and hydrogen peroxide solution (O), indicating that they were very stable; SEQ ID NO: 26 was also extremely stable in artificial intestinal juice (X); EGF was not retained in both the gastric juice and intestinal juice, indicating that it was unstable in the gastric juice and intestinal juice, and where EGF was applied externally after disinfection with povidone-iodine solution and hydrogen peroxide solution, EGF was also destroyed.

Example 10: Effect of the Compound of SEQ ID NO: 1 on Aspirin-Induced Gastric Ulcer in Rats Method: After adaptive feeding, SD rats were divided into three groups (10 rats in each group) by Excel-based complete randomization, namely, a control group, a model group, and a the compound of SEQ ID NO: 1 (0.3 mg/kg) group. After the animals were grouped, they were given corresponding treatments (the control group and the model group were given the same volume of purified water, and the SEQ ID NO: 1 group was given corresponding drug treatment) once a day for 8 consecutive days. On the 7th day after administration, all the animals were fasted for 24 h with free access to water. On the 8th day, except for the control group, the rats in the SEQ ID NO: 1 group and the model group were orally given 250 mg/kg aspirin solution for modeling 30 min after compound administration (or given water). 4 h after modeling, the animals were sacrificed, the cardia was ligated, the pylorus was occluded, and the whole stomach was removed. 8 mL of 1% formaldehyde solution was injected into the gastric lumen, the pylorus was ligated, and the stomach was taken out and immediately immersed in 1% formaldehyde solution for fixation. After 30 min, the stomach was cut open along the greater curvature, the content of the stomach was cleaned off with normal saline, and after the stomach was laid flat, the stomach was observed, and panoramic photos were taken to measure the ulcer area.

Results: Oral gavage of the compound of SEQ ID NO: 1 (0.3 mg/kg) once a day for 8 consecutive days had no obvious effects on the weight change of the aspirin-induced gastric ulcer model rats. the compound of SEQ ID NO: 1 reduced bleeding points in the stomach of the aspirin-induced gastric ulcer model rats and significantly reduced the area of gastric ulcer in the rats. Table 10 showed the effect of the compound of SEQ ID NO: 1 on aspirin-induced gastric ulcers in rats.

TABLE 10

Effect of the compound SEQ ID NO: 1 on aspirin-induced gastric ulcer in rats.

| Group/dose | Ulcer area (mm$^2$) |
|---|---|
| Control group: | 7.42 ± 7.32 |
| Model group: | 140.36 ± 82.40## |
| SEQ ID NO. 1 group: | 20.55 ± 10.45** |

Note:
p < 0.01, compared with the control group; and
**p < 0.01, compared with the model group, Although the above examples are disclosed in the present invention, the embodiments of the present invention are not limited to the above examples, and any other changes, modifications, substitutions, combinations, and simplifications that do not depart from the present invention should be equivalent replacements and are included in the scope of protection of the present invention.

What is claimed is:

1. A synthesized compound or physiologically compatible salt thereof, wherein the compound is selected from the group consisting of:
    Pro-Ala-Ala-Glu-Pro-Val-Pro-Leu-Val-Lys-Gln-Asp (SEQ ID No: 1);
    Pro-Ala-Ala-Glu-Pro-Val-Pro-Leu-Val-Lys (SEQ ID No: 3);
    Pro-Ala-Ala-Gln-Pro-Val-Pro-Leu-Val-Lys-Gln-Asp (SEQ ID No: 10);
    Pro-Ala-Ala-Asp-Pro-Val-Pro-Leu-Val-Lys-Gln-Asp (SEQ ID No: 11);
    Pro-Ala-Ala-Glu-Pro-Val-Pro-Leu (SEQ ID No: 26);
    Ala-Glu-Pro-Val-Pro-Leu-Val-Lys-Gln-Asp (SEQ ID No: 27);
    Pro-Val-Pro-Leu-Val-Lys-Gln-Asp (SEQ ID No: 28);
    Ala-Glu-Pro-Val-Pro-Leu (SEQ ID No: 30);
    Glu-Pro-Val-Pro-Leu (SEQ ID No: 31);
    Glu-Pro-Val-Pro-Leu-Val-Lys-Gln-Asp (SEQ ID No: 38);
    Pro-Ala-Gly-Glu-Pro-Val-Pro-Leu-Val-Lys-Gln-Asp (SEQ ID No: 48);
    Pro-Ala-Ala-Glu-Pro-Val-Pro-Leu-Val-Lys-Glu-Asp (SEQ ID No: 57);
    Pro-Ala-Ala-Glu-Pro-Val-Pro-Leu-Ile-Lys-Gln-Asp (SEQ ID No: 64);
    Pro-Ala-Ala-Glu-Pro-Val-Pro-Leu-Val-Arg-Gln-Asp (SEQ ID No: 66); and
    Pro-Ala-Ala-Val-Pro-Val-Pro-Leu-Val-Lys-Gln-Asp (SEQ ID No: 67).

2. The compound or physiologically compatible salt thereof according to claim 1, wherein the compound is selected from the group consisting of:
    Pro-Ala-Ala-Glu-Pro-Val-Pro-Leu-Val-Lys-Gln-Asp (SEQ ID No: 1);
    Pro-Ala-Ala-Glu-Pro-Val-Pro-Leu (SEQ ID No: 26); and
    Ala-Glu-Pro-Val-Pro-Leu (SEQ ID No: 30).

3. A pharmaceutical composition, a food composition, a health care or cosmetic composition or commodity composition, said composition comprising the compound or a physiologically compatible salt thereof according to claim 1 and a physiologically acceptable carrier.

4. A method of repairing skin wounds or mucosal damage, comprising administering to the subject in need thereof the compound or physiologically compatible salt thereof according to claim 1 in the preparation of a medicament for repairing skin wounds or mucosal damage.

5. The method according to claim 4, wherein the mucosal damage is mucosal damage in a cavity comprising the digestive system or respiratory system.

6. The method according to claim 5, wherein the mucosal damage of the digestive system is related to oral, esophageal, or gastrointestinal disease.

7. The method according to claim 6, wherein
the oral disease is oral ulcer, stomatitis, gingivitis, or periodontitis;
the esophageal disease is esophagitis, or esophageal ulcer; or
the gastrointestinal disease is chronic gastritis, chronic atrophic gastritis, acute gastritis, gastroduodenal ulcer, functional gastrointestinal diseases, dyspepsia, precancerous lesions, digestive system tumors, gastrointestinal bleeding, gastroesophageal reflux disease, acute and chronic enteritis, ulcerative colitis, Crohn's disease, or mucosal injuries caused by radiotherapy and/or chemotherapy.

8. The method according to claim 5, wherein the mucosal damage of the digestive system is mucosal damage caused by an irritant substance or a drug or by a stress state.

9. The method according to claim 4, wherein the skin wounds are related to epidermal inflammation, mechanical and surgical wound, burns and scalds, ulcers, fistulas, bedsores, or skin injuries caused by radiotherapy and/or chemotherapy.

10. A method for regulating the proliferation and differentiation of stem cells, comprising administering to the subject in need thereof the compound or physiologically compatible salt thereof according to claim 1.

11. A method for preventing, alleviating or treating a gastrointestinal disease or eliminating inflammatory edema, comprising administering to the subject in need thereof the compound or physiologically compatible salt thereof according to claim 1.

* * * * *

SEQUENCE LISTING

```
<160> NUMBER OF SEQ ID NOS: 73

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Pro Ala Ala Glu Pro Val Pro Leu Val Lys Gln Asp
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Ala Ala Glu Pro Val Pro Leu Val Lys Gln Asp
1               5                   10
```

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Pro Ala Ala Glu Pro Val Pro Leu Val Lys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Pro Ala Ala Glu Gly Val Pro Leu Val Lys Gln Asp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Pro Ala Ala Glu Pro Val Gly Leu Val Lys Gln Asp
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Pro Ala Ala Glu Pro Val Gly Ala Val Lys Gln Asp
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Pro Ala Ala Glu Pro Val Gly Val Val Lys Gln Asp
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 8

Pro Ala Ala Glu Gly Val Gly Leu Val Lys Gln Asp
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Ala Ala Glu Gly Val Gly Leu
1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Pro Ala Ala Gln Pro Val Pro Leu Val Lys Gln Asp
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Pro Ala Ala Asp Pro Val Pro Leu Val Lys Gln Asp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Pro Ala Ala Glu Pro Val Pro Phe Val Lys Gln Asp
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Pro Ala Ala Glu Pro Val Pro Tyr Val Lys Gln Asp
1               5                   10

<210> SEQ ID NO 14
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Pro Ala Ala Glu Pro Val Gly Leu Val Lys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Pro Ala Ala Glu Pro Val Gly Val Val Lys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Pro Ala Ala Glu Pro Val Ala Leu Val Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Pro Ala Ala Glu Pro Val Ala Val Val Lys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Pro Ala Ala Glu Ala Val Pro Leu Val Lys Gln Asp
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Pro Ala Ala Glu Pro Val Ala Leu Val Lys Gln Asp
```

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Pro Ala Ala Glu Ala Val Ala Leu Val Lys Gln Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Ala Ala Glu Pro Val Pro Leu Val Lys Gln Asp
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Pro Ala Ala Glu Pro Val Pro Phe Val Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Pro Ala Ala Glu Pro Val Pro Tyr Val Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Pro Ala Ala Glu Pro Val Gly Phe Val Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 25

Pro Ala Ala Glu Pro Val Ala Phe Val Lys
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Pro Ala Ala Glu Pro Val Pro Leu
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Glu Pro Val Pro Leu Val Lys Gln Asp
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Pro Val Pro Leu Val Lys Gln Asp
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Pro Ala Ala Glu Pro Val Pro
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Glu Pro Val Pro Leu
1               5

<210> SEQ ID NO 31
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Pro Val Pro Leu
1               5

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Pro Val Pro Leu
1

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Ala Glu Pro Val Pro Leu
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Pro Ala Ala Glu Pro Val
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Pro Ala Ala Glu Pro
1               5

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36
```

```
Pro Ala Ala Glu
1

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Ala Glu Pro Val Pro Leu Val Lys Gln Asp
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Pro Val Pro Leu Val Lys Gln Asp
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Val Pro Leu Val Lys Gln Asp
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Pro Leu Val Lys Gln Asp
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Pro Ala Ala Glu Pro Val Pro Ile Val Lys
1               5                   10

<210> SEQ ID NO 42
<211> LENGTH: 10
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 42

Pro Ala Ala Glu Pro Val Pro Val Val Lys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Pro Ala Ala Glu Pro Val Pro Met Val Lys
1               5                   10

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Glu Pro Val Pro
1               5

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Glu Pro Val
1

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Pro Ala Ala Asn Pro Val Pro Leu Val Lys Gln Asp
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Pro Ala Ala Leu Pro Val Pro Leu Val Lys Gln Asp
1               5                   10

```
<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Pro Ala Gly Glu Pro Val Pro Leu Val Lys Gln Asp
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Pro Ala Pro Glu Pro Val Pro Leu Val Lys Gln Asp
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Pro Ala Ala Glu Pro Val Pro Leu Val Lys Gln Asn
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Pro Ala Ala Glu Pro Val Pro Leu Val Val Gln Asp
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Pro Ala Ala Glu Pro Val Pro Val Val Lys Gln Asp
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53
```

```
Pro Ala Ala Glu Pro Val Pro Ile Val Lys Gln Asp
1               5                   10
```

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Pro Ala Ala Glu Pro Val Pro Met Val Lys Gln Asp
1               5                   10
```

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Pro Leu Ala Glu Pro Val Pro Leu Val Lys Gln Asp
1               5                   10
```

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Pro Ile Ala Glu Pro Val Pro Leu Val Lys Gln Asp
1               5                   10
```

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Pro Ala Ala Glu Pro Val Pro Leu Val Lys Glu Asp
1               5                   10
```

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Pro Ala Ala Glu Pro Val Pro Leu Val Lys Asn Asp
1               5                   10
```

<210> SEQ ID NO 59
<211> LENGTH: 12
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 59

Pro Ala Ala Glu Pro Val Pro Leu Val Lys Asp Asp
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Pro Ala Ala Glu Pro Val Pro Leu Val Lys Gln Glu
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Pro Ala Leu Glu Pro Val Pro Leu Val Lys Gln Asp
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Pro Ala Ile Glu Pro Val Pro Leu Val Lys Gln Asp
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Pro Ala Ala Glu Pro Val Pro Leu Leu Lys Gln Asp
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Pro Ala Ala Glu Pro Val Pro Leu Ile Lys Gln Asp
1               5                   10
```

```
<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Pro Ala Ala Glu Pro Val Pro Leu Met Lys Gln Asp
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Pro Ala Ala Glu Pro Val Pro Leu Val Arg Gln Asp
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Pro Ala Ala Val Pro Val Pro Leu Val Lys Gln Asp
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Val Pro Leu Val Lys Gln Asp
1               5

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gly Ala Ala Val Pro Val Pro Leu Val Lys Gln Asp
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 70

Gly Ala Gly Val Pro Val Pro Leu Val Lys Gln Asp
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gly Ala Gly Val Gly Val Pro Leu Val Lys Gln Asp
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Pro Ala Ala Glu Pro Val Ala Phe Val Lys Gln Asp
1               5                   10

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Val Pro Leu Val
1
```